United States Patent
Zhang et al.

(10) Patent No.: US 12,054,488 B2
(45) Date of Patent: Aug. 6, 2024

(54) PYRAZOLOPYRIMIDINE COMPOUND AND PREPARATION METHOD THEREFOR AND USE THEREOF IN PREPARATION OF ANTI-CANCER DRUG

(71) Applicant: SUZHOU RAYMON PHARMACEUTICALS COMPANY, LTD., Suzhou (CN)

(72) Inventors: Fei Zhang, Suzhou (CN); Zixia Feng, Suzhou (CN)

(73) Assignee: SUZHOU RAYMON PHARMACEUTICALS COMPANY, LTD., Suzhou (CN)

(*) Notice: Subject to any disclaimer, the term of this patent is extended or adjusted under 35 U.S.C. 154(b) by 689 days.

(21) Appl. No.: 17/280,245

(22) PCT Filed: Sep. 25, 2019

(86) PCT No.: PCT/CN2019/107734
§ 371 (c)(1),
(2) Date: Mar. 26, 2021

(87) PCT Pub. No.: WO2020/063636
PCT Pub. Date: Apr. 2, 2020

(65) Prior Publication Data
US 2021/0340146 A1 Nov. 4, 2021
US 2022/0106316 A2 Apr. 7, 2022

(30) Foreign Application Priority Data
Sep. 27, 2018 (CN) .......................... 201811146369.8

(51) Int. Cl.
*C07D 487/04* (2006.01)
*A61K 31/407* (2006.01)
(Continued)

(52) U.S. Cl.
CPC .......... *C07D 487/04* (2013.01); *A61K 31/407* (2013.01); *A61K 31/5377* (2013.01);
(Continued)

(58) Field of Classification Search
CPC ..... C07D 487/04; C07D 239/42; A61P 35/00; A61P 35/02; A61K 31/407; A61K 31/5377
See application file for complete search history.

(56) References Cited

U.S. PATENT DOCUMENTS

2022/0389017 A1* 12/2022 Zhang .................... A61P 35/00

FOREIGN PATENT DOCUMENTS

| CN | 105143209 A | 12/2015 |
| WO | 0183456 A1 | 11/2001 |

(Continued)

OTHER PUBLICATIONS

CAS Substance Detail for Registry No. 1062172-60-4. Accessed Dec. 5, 2023. (Year: 2023).*

(Continued)

*Primary Examiner* — Clinton A Brooks
*Assistant Examiner* — Kyle Nottingham
(74) *Attorney, Agent, or Firm* — HAUPTMAN HAM, LLP

(57) ABSTRACT

Provided in the present disclosure is a type of pyrazolopyrimidine compound as shown in formula (I) or a pharmaceutically acceptable salt thereof, and a preparation method thereof and the use of same in the preparation of a drug for treating or preventing cancers. Such a compound is a new-type PI3K inhibitor and has an excellent inhibitory activity, and can hopefully be used for treating a variety of malignant tumors.

(Continued)

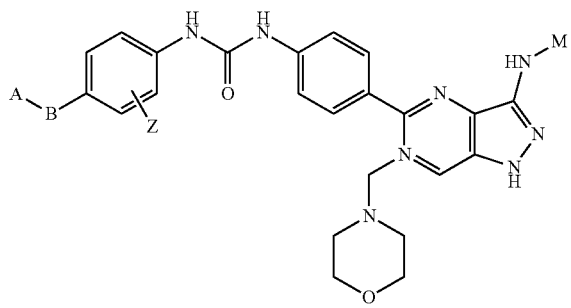

(52) U.S. Cl.
CPC ............... *A61P 35/00* (2018.01); *A61P 35/02* (2018.01); *C07D 239/42* (2013.01)

(56) References Cited

FOREIGN PATENT DOCUMENTS

| WO | WO-2007139856 A2 | * | 12/2007 | ............ C07D 487/04 |
| WO | WO-2008115974 A2 | * | 9/2008 | ................ A61P 1/18 |
| WO | 2010118367 A2 | | 10/2010 | |
| WO | WO-2014151616 A1 | * | 9/2014 | ............ A61K 31/444 |

OTHER PUBLICATIONS

International Search Report issued in corresponding International Application No. PCT/CN2019/107734; mailed Dec. 31, 2019; State Intellectual Property Office of the P.R. China, Beijing, China, 7 pgs.
Written Opinion issued in corresponding International Application PCT/CN2019/107734; mailed Dec. 31, 2019; State Intellectual Property Office of the P.R. China, Beijing, China, 5 pgs.

* cited by examiner

21 Claims, 1 Drawing Sheet

(51) Int. Cl.
*A61K 31/5377* (2006.01)
*A61P 35/00* (2006.01)
*A61P 35/02* (2006.01)
*C07D 239/42* (2006.01)

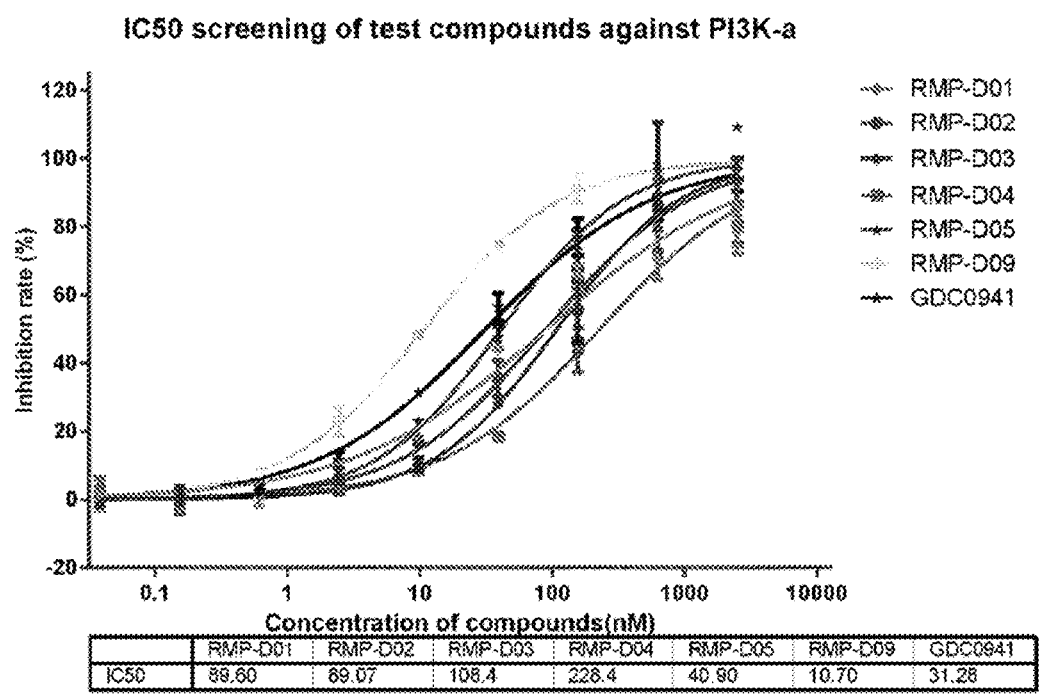

PYRAZOLOPYRIMIDINE COMPOUND AND PREPARATION METHOD THEREFOR AND USE THEREOF IN PREPARATION OF ANTI-CANCER DRUG

RELATED APPLICATIONS

The present application is a National Phase of International Application Number PCT/CN2019/107734 filed Sep. 25, 2019 and claims priority to Chinese Application Number 201811146369.8 filed Sep. 27, 2018.

TECHNICAL FIELD OF THE INVENTION

The present disclosure belongs to the field of medicinal chemistry, and in particular relates to a class of pyrazolopyrimidine compounds and a preparation method thereof. The pyrazolopyrimidine compounds have phosphatidylinositol 3-kinase (PI3K) inhibitory activity and can be used to prepare drugs for preventing and treating tumors.

BACKGROUND OF THE INVENTION

PI3K is an intracellular phosphatidylinositol kinase. Lewis C. Cantley, professor of cancer biomedicine at Weill Cornell Medical College, discovered the phosphatidylinositol 3-kinase (PI3K) signaling pathway and clarified its key role in tumor development. The PI3K signaling pathway is usually activated by receptors on the cell surface, such as receptor tyrosine kinases, GPCRs, and some oncogenes, such as RAS. The activated p110 subunit catalyzes the conversion of PIP2 to PIP3 and activates Akt activity. Akt will further transmit signals to downstream molecules, such as mTORC1, GSK3, and BCL-2 to regulate different cellular physiological processes. mTORC2 activates the Akt molecules through Ser 473 phosphorylation. In contrast, PTEN can dephosphorylate PIP3 into PIP2. The downstream signaling pathways of PI3K molecules are more complex, including some feedback loops. Each of the four catalytic isomers of class I PI3K preferentially regulates specific signal transduction and tumor cell survival, depending on the type of malignant tumor and its genetic or epigenetic changes. For example, p110α is essential for the growth of tumor cells driven by PIK3CA mutations or oncogene RAS and receptor tyrosine kinases; p110β mediates the occurrence of PTEN-deficient tumors; and p110δ is highly expressed in white blood cells, so that it becomes an ideal target for the treatment of hematological malignancies.

In the late 1980s, PI3 kinase (PI3K) was discovered to be an enzyme that phosphorylates the 3-position of the inositol ring of phosphatidylinositol (D. Whitman et al. (1988) *Nature,* 332664). PI3K was originally thought to be a single enzyme, but it has now been clarified that there are multiple subtypes in PI3K, and PI3Kα is one of them. PI3Kα has high-frequency activating mutations in breast cancer, which is closely related to the development and drug resistance of breast cancer, and has become an important target for the treatment of breast cancer.

On Sep. 14, 2017, the U.S. FDA accelerated the approval of Bayer Healthcare Pharmaceuticals' Aliqopa® (Copanlisib), Aliqopa® is the trade name. It is used to treat patients suffering from recurrent follicular lymphoma.

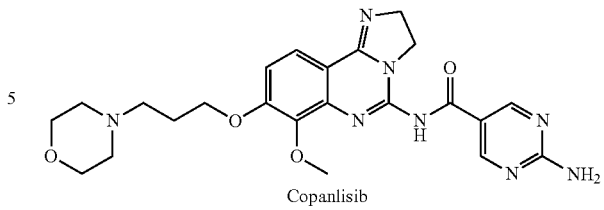

Copanlisib

Copanlisib is a phosphatidylinositol 3-kinase (PI3K) inhibitor, which has good inhibitory activity against the PI3K-α and PI3K-δ subtypes expressed in malignant B cells.

There are limited types of PI3Kα inhibitors and the efficacy of PI3Kα inhibitors in clinical trials varies greatly among individuals. It is desired to discover new PI3Kα inhibitors and biomarkers for efficacy prediction.

In the first half of 2019, the U.S. FDA announced that it has approved Piqray (alpelisib) developed by Novartis (NVS.US) to be used in combination with endocrine therapy fulvestrant to treat patients with HR+/HER2-advanced or metastatic breast cancer carrying PIK3CA gene mutations. These patients continue to get worse after receiving endocrine therapy. This is the first PI3K inhibitor approved by the FDA for the treatment of breast cancer. The tumors of patients with metastatic breast cancer have spread to other parts of the body, and the most common metastatic organs include bones, lungs, liver, and brain. In HR+/HER2-advanced breast cancer, changes in the PI3K pathway are the most common cause of tumor deterioration, disease progression, and drug resistance in treatment. About 40% of HR+/HER2-advanced breast cancer patients carry PIK3CA gene mutations. Piqray is an oral small molecule α-specific PI3K inhibitor developed by Novartis, namely PI3Kα inhibitor. In breast cancer cell lines carrying PIK3CA gene mutations, it has shown the potential to inhibit the PI3K pathway and has the effect of inhibiting cell proliferation. The present disclosure also uses PI3Kα as the starting point for target research of new drugs, especially in China, there is no PI3Kα inhibitor invented in China for the treatment of malignant tumors. The structure of the innovative research of the present disclosure will fill this gap in China. Such as the final listing will have significant social and economic benefits.

SUMMARY OF THE INVENTION

The technical problem to be solved by the present disclosure is to provide a class of pyrazolopyrimidine compounds having phosphatidylinositol 3-kinase (PI3K) inhibitory activity.

The present disclosure also provides an intermediate for preparing the above pyrazolopyrimidine compounds.

The present disclosure also provides a method for preparing the above pyrazolopyrimidine compounds.

In order to solve the above technical problems, the present disclosure adopts the following technical solution:

A pyrazolopyrimidine compound represented by Formula (I), or a stereoisomer, a pharmaceutically acceptable salt, a solvate or a crystal thereof (sometimes collectively referred to herein as "compounds of the present disclosure"):

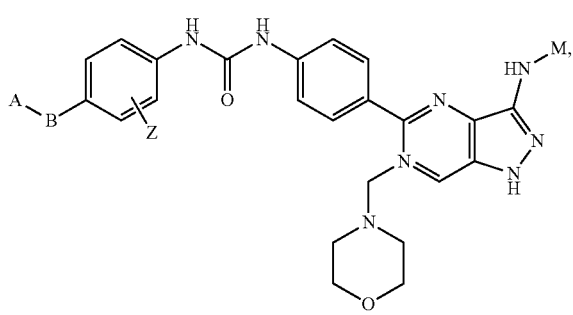

(I)

in the formula, A is selected from the group consisting of —OH, —NH$_2$, —SH,

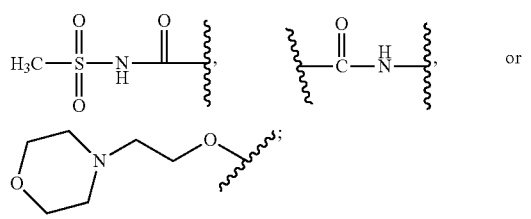

B is —C$_n$H$_{2n}$—, n is 1, 2, 3 or 4; wherein, when A is

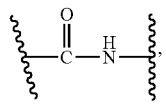

one end thereof is connected to B, and the other end is connected to a carbon atom on a phenyl ring to which B is connected;

Z is selected from the group consisting of hydrogen, hydroxy, C$_{1-3}$ alkyl, fluorine, chlorine, bromine, or C$_{1-3}$ alkyl substituted by one or more selected from fluorine, chlorine and bromine; and M is H, —CH$_3$ or —CH$_2$CH$_3$.

Further, Z is preferably selected from the group consisting of hydrogen, hydroxyl, fluorine, chlorine, bromine, methyl, ethyl, isopropyl, trifluoromethyl, or pentafluoroethyl, etc.

According to some preferred and specific aspects of the present disclosure, the structure of the pyrazolopyrimidine compound is represented by the following Formula (I-a):

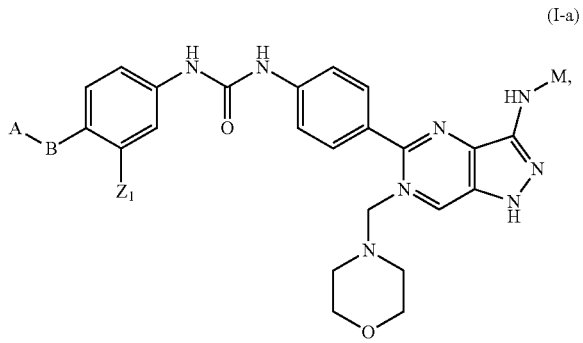

(I-a)

wherein, A, B and M are defined the same as above, and Z$_1$ is defined the same as Z. Further, Z$_1$ is selected from the group consisting of hydrogen, hydroxyl, fluorine, chlorine, bromine, methyl, ethyl, isopropyl, trifluoromethyl, or pentafluoroethyl, etc.

According to a further implementation of the present disclosure, B may be linear or branched, and there is no particular limitation.

According to some preferred aspects of the present disclosure, B is selected from the group consisting of —CH$_2$—, —CH$_2$CH$_2$—, —CH$_2$CH$_2$CH$_2$—, —CH(CH$_3$)—, —CH(CH$_3$)CH$_2$—, —C(CH$_3$)$_2$— or —CH$_2$C(CH$_3$)$_2$—. Especially preferably, B is —CH$_2$— or —C(CH$_3$)$_2$—.

According to some preferred aspects of the present disclosure, when A is

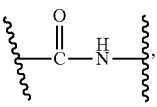

C thereof is connected to B, N is connected to a carbon atom on a phenyl ring to which B is connected, and A, B and the carbon atom to which they are connected together form a 5- to 7-membered ring. In some specific implementations of the present disclosure, a carbon atom connected to the N atom of A and a carbon atom connected to B are attached in adjacent positions of a phenyl ring. Further preferably, B is —C(CH$_3$)$_2$—.

According to some preferred aspects of the present disclosure, B is —CH$_2$—, and A is —OH,

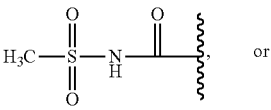

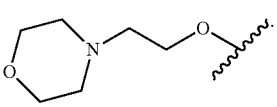

According to some other preferred aspects of the present disclosure, B is —C(CH$_3$)$_2$—, and A is —OH or

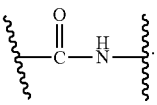

According to some preferred and specific aspects of the present disclosure, the pyrazolopyrimidine compound is selected from compounds represented by the following formulas:

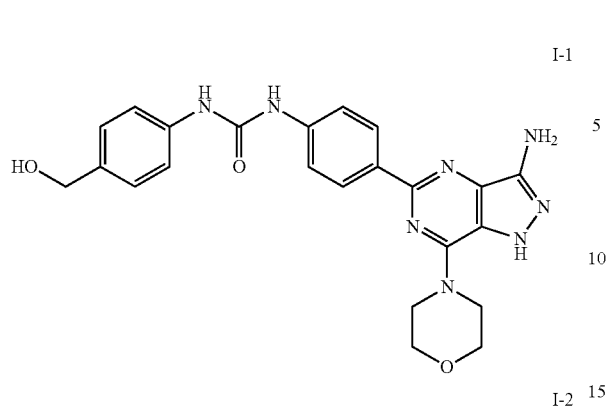

I-1

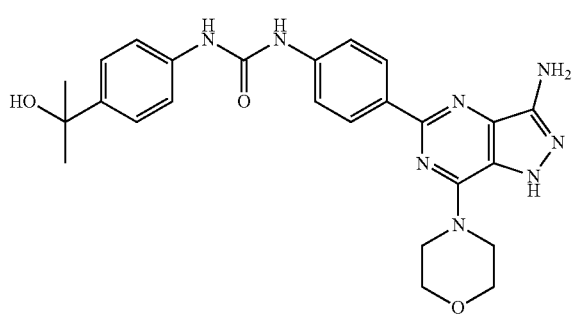

I-2

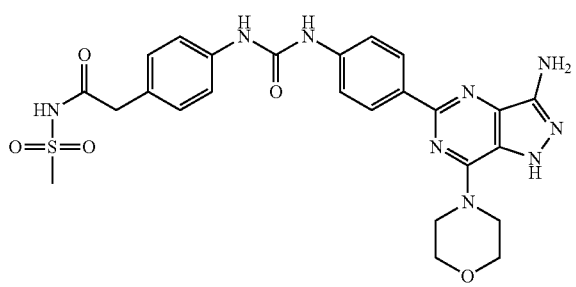

I-3

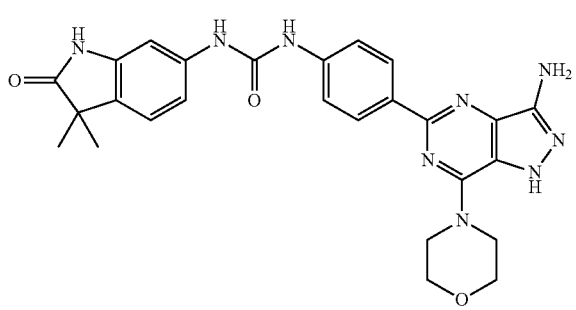

I-4

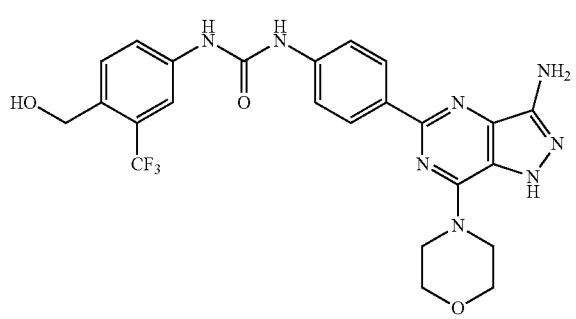

I-5

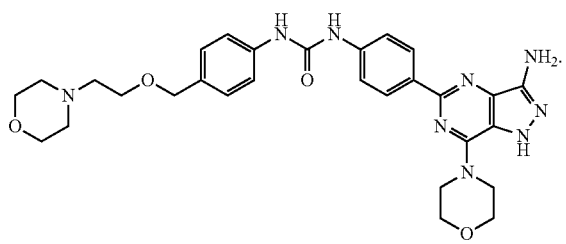

I-6

The present disclosure further provides a pharmaceutical composition containing one or more of pyrazolopyrimidine compounds, or the stereoisomer, the pharmaceutically acceptable salt, the solvate or the crystal thereof provided above. In some implemented examples, the composition further contains a pharmaceutical acceptable carrier.

The present disclosure provides use of the above pyrazolopyrimidine compound, or the stereoisomer, the pharmaceutically acceptable salt, the solvate or the crystal thereof, or a pharmaceutical composition containing the pyrazolopyrimidine compound in preparation of a drag for treating and/or preventing phosphatidylinositol 3-kinase (PI3K)-mediated diseases.

The phosphatidylinositol 3-kinase (PI3K)-mediated diseases generally comprise cancer. The cancer comprises, but not be limited to, renal carcinoma, liver cancer, colon cancer, gastrointestinal stromal tumor, non-small cell lung cancer, breast cancer, pancreatic cancer, glioma, lymphoma, fibrosarcoma, ovarian cancer, leukemia and prostate cancer, etc.

The present disclosure further provides use of the pharmaceutical composition in preparation of a drag for treating and/or preventing cancer and a method for treating and/or preventing cancer using the pharmaceutical composition.

In the pharmaceutical composition according to the present disclosure, the compounds of the present disclosure are preferably present in a therapeutically effective amount.

The pharmaceutical acceptable carrier in the above pharmaceutical composition may be, for example, a pharmaceutically acceptable diluent, excipient, filler, binder, disintegrant, absorption enhancer, surfactant, lubricant, flavor, sweeteners, etc.

The drug prepared by using the compound of the present disclosure as an active ingredient can be in various forms such as tablets, powders, capsules, granules, oral liquids and injection preparations. The dosage form of the pharmaceutical composition is preferably a tablet, capsule or injection.

The above-mentioned various dosage forms of drug can be prepared according to conventional methods in the field of pharmacy.

The present disclosure further provides an intermediate for preparing the pyrazolopyrimidine compound represented by Formula (I), or the stereoisomer, the pharmaceutically acceptable salt, the solvate or the crystal thereof, and the intermediate has a structure represented by Formula (II):

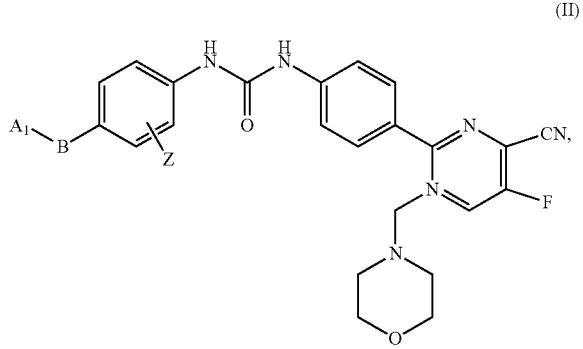

(II)

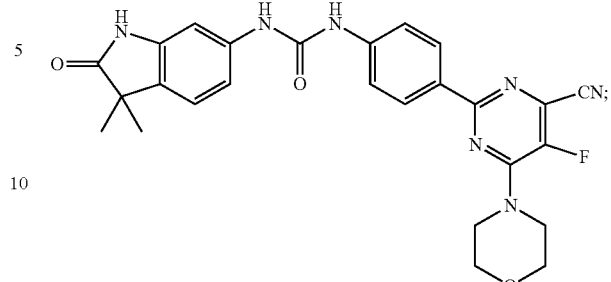

(II-4)

in Formula (II), $A_1$ is tert-butyldimethylsiloxy (TBSO) or $A_1$ is the same as A; B and Z are respectively the same as B and Z in Formula (I).

According to some specific aspects of the present disclosure, the intermediate for preparing the pyrazolopyrimidine compound of the present disclosure, or the stereoisomer, the pharmaceutically acceptable salt, the solvate or the crystal thereof, comprises:

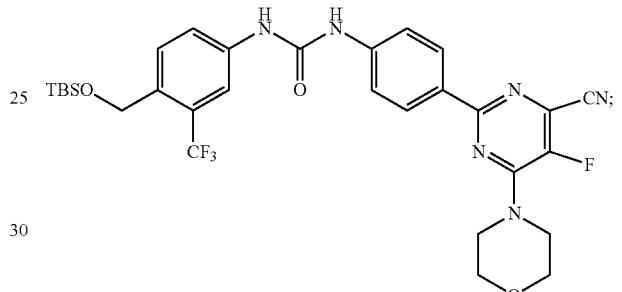

(II-5)

(II-1)

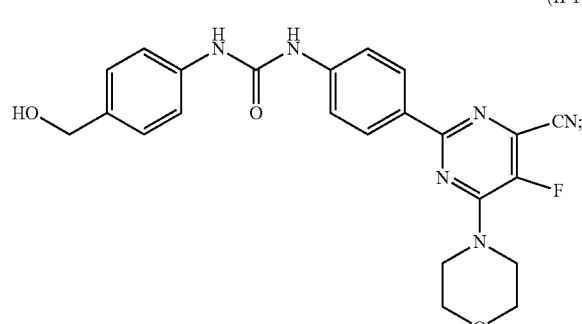

(II-2), (II-3)

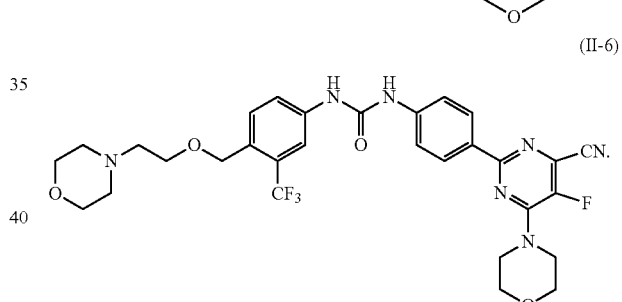

(II-6)

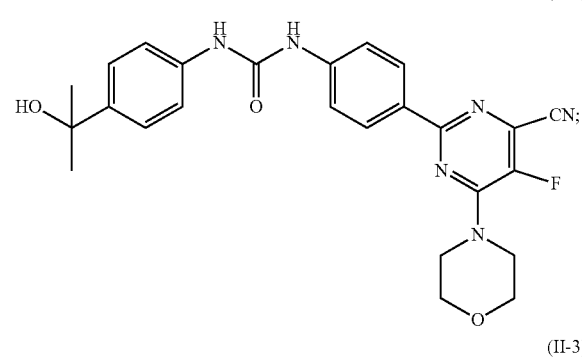

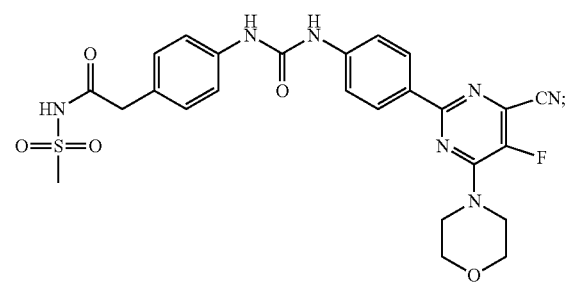

The present disclosure further provides a method for preparing the pyrazolopyrimidine compound represented by Formula (I), or the stereoisomer, the pharmaceutically acceptable salt, the solvate or the crystal thereof, and the preparation method comprises a step of reacting the intermediate represented by Formula (II) with hydrazine hydrate.

In some implementations of the present disclosure, the reaction of the intermediate represented by Formula (II) with hydrazine hydrate is carried out at 20-100° C., preferably at 30-95° C., more preferably at 40-90° C., further preferably at 55-80° C., and even more preferably at 60-75° C. According to some preferred and specific aspects of the present disclosure, the reaction of the intermediate represented by Formula (II) with hydrazine hydrate is carried out at 65-70° C.

Further, the intermediate represented by Formula (II) may be prepared by reacting

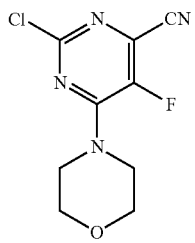 [SMILES: N#Cc1nc(Cl)nc(N2CCOCC2)c1F]

with a compound represented by Formula (III)

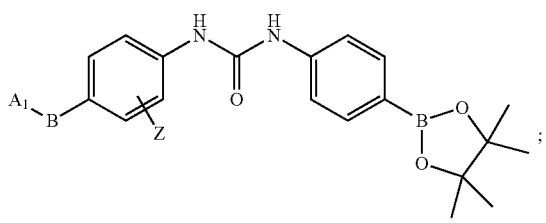

and in Formula (III), $A_1$, B and Z are defined the same as in Formula (II).

According to some preferred aspects of the present disclosure, in the process of preparing the intermediate represented by Formula (II), the reaction is carried out under alkaline conditions at a temperature of 30-120° C., and optionally under an inert atmosphere. More preferably, in the process of preparing the intermediate represented by Formula (II), the reaction is carried out at a temperature of 40-110° C., preferably at a temperature of 50-105° C., more preferably at a temperature of 60-100° C., and even more preferably at a temperature of 70-95° C. According to some specific aspects of the present disclosure, in the process of preparing the intermediate represented by Formula (II), the reaction is carried out at a temperature of 85-90° C.

According to some implementations of the present disclosure, the inert atmosphere is a nitrogen atmosphere.

According to some implementations of the present disclosure, the alkaline condition is formed by adding an alkaline substance, and the alkaline substance is selected from the group consisting of potassium acetate, potassium carbonate, potassium phenoxide, potassium phosphate, potassium tert-butoxide, sodium carbonate, sodium bicarbonate, sodium tert-butoxide, sodium methoxide, sodium ethoxide, triethylamine, tri-n-butylamine, diisopropylethylamine, and combinations thereof. According to some preferred and specific aspects of the present disclosure, the alkaline substance is sodium bicarbonate.

Due to the implementation of the above technical solutions, the present disclosure has the following advantages over the prior art:

The present disclosure provides a novel pyrazolopyrimidine compound, which has excellent PI3K inhibitory activity, and can be applied to treat phosphoinositide 3-kinase (PI3K)-mediated diseases, and provide more and better drug choices for cancer treatment. In addition, compared with existing PI3K inhibitors, the pyrazolopyrimidine compound of the present disclosure has a simple structure and a relatively low preparation cost.

BRIEF DESCRIPTION OF THE DRAWINGS

FIG. 1 shows the relationship curves of the inhibitory rates of Compound I-1 to Compound I-6 and the positive control compound GDC-0941 on PI3Kα.

DETAILED DESCRIPTION OF EXEMPLARY EMBODIMENTS

Definition of Terms

Unless otherwise defined, all technical and scientific terms used herein have the same meaning as commonly understood by one of ordinary skill in the art to which this disclosure belongs.

The term "isomer" refers to an isomer produced by the different arrangement of atoms in a molecule in space, and includes cis-trans isomers, enantiomers and conformational isomers. All stereoisomers are within the scope of the present disclosure. The compounds of the present disclosure may be a single stereoisomer or a mixture of other isomers such as a racemate, or a mixture of all other stereoisomers.

The term "salt" refers to a pharmaceutically acceptable salt formed by a compound of the present disclosure with an acid, the acid may be an organic or inorganic acid, specifically selected from the group consisting of phosphoric acid, sulfuric acid, hydrochloric acid, hydrobromic acid, citric acid, maleic acid, malonic acid, mandelic acid, succinic acid, fumaric acid, acetic acid, lactic acid, nitric acid, sulfonic acid, p-toluenesulfonic acid, malic acid, methanesulfonic acid or analogues thereof.

The term "solvate" refers to a form of a compound of the present disclosure that forms a solid or liquid complex by coordination with a solvent molecule. Hydrates are a special form of solvates in which coordination occurs with water. Within the scope of the present disclosure, the solvate is preferably a hydrate.

The term "crystal" refers to the various solid forms formed by the compounds described herein, including crystalline forms and amorphous forms.

The following embodiments may enable those skilled in the art to fully understand the present disclosure, but do not limit the present disclosure in any way. The structures of all compounds were confirmed by $^1$H-NMR or MS.

The compounds used in the embodiments are abbreviated as follows:

DBU: 1,8-diazabicyclo[5.4.0]undec-7-ene; DMF: N,N-dimethylformamide

THF: tetrahydrofuran;

Pd(dppf)Cl$_2$: [1,1'-bis(diphenylphosphino)ferrocene]dichloropalladium;

DTT: dithiothreitol; ATP: adenosine triphosphate; TK: tyrosine kinase;

HEPES: 2-[4-(2-hydroxyethyl)-1-piperazinyl]ethanesulfonic acid.

Embodiment 1: Preparation of Compound I-1

Compound I-1 was synthesized through the following route:

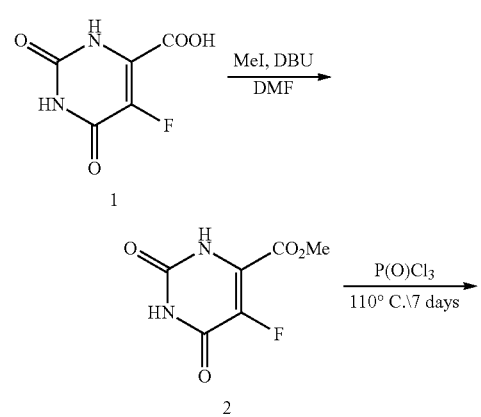
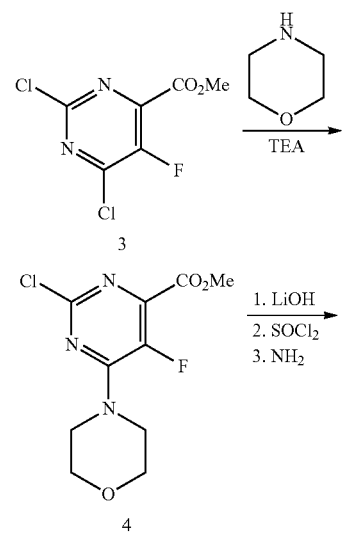
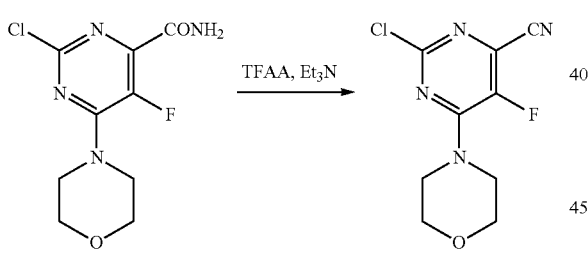
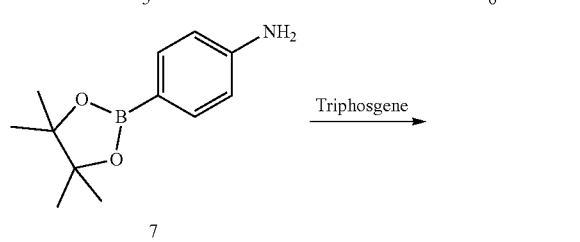
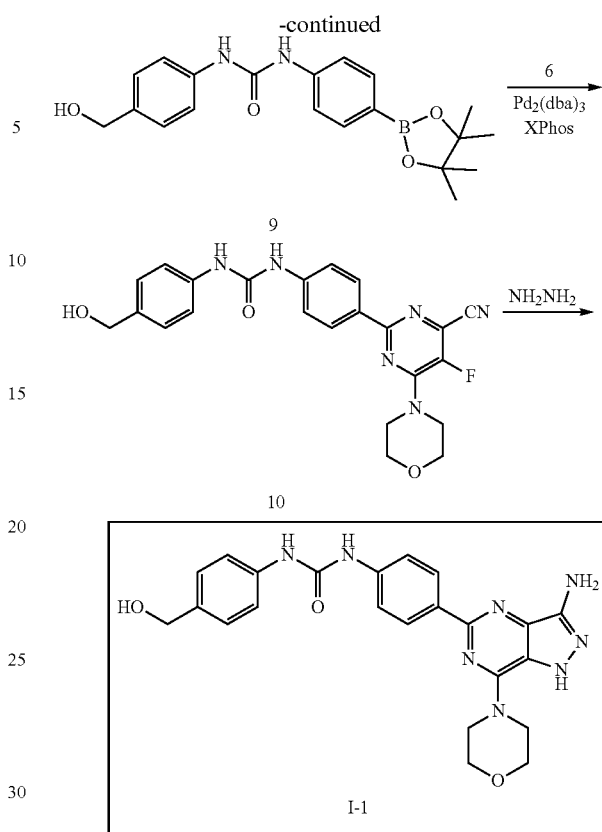

1.1. Synthesis of Compound 2

Compound 2: methyl 5-fluoro-2,6-dioxo-1,2,3,6-tetrahydropyrimidine-4-carboxylate

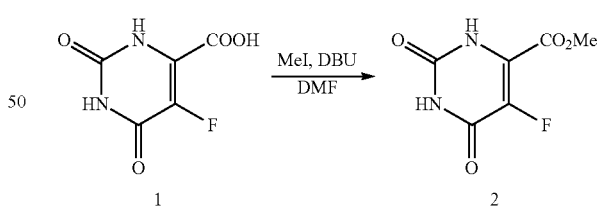

5-fluoroorotic acid (Compound 1) (40 g, 0.23 mol) was dissolved in N,N-dimethylformamide (500 mL), DBU (35.0 g, 0.23 mol) was slowly added dropwise, and the system was stirred at room temperature for 1 h, then iodomethane (32.0 g, 0.23 mol) was slowly added dropwise, and the system was stirred at 60° C. for 4 h. Upon the reaction completion, 100 mL of ice water was added with stirring to precipitate solids, filtered, and the filter cake was washed with water (100 mL×3) and vacuum dried to give Compound 2 (30 g, yield=70%). Measured: $^1$H NMR (CDCl$_3$, 400 MHz): δ11.85 (s, 1H), 10.84 (s, 1H), 3.88 (s, 3H).

1.2. Synthesis of Compound 3

Compound 3: methyl 2,6-dichloro-5-fluoropyrimidine-4-carboxylate

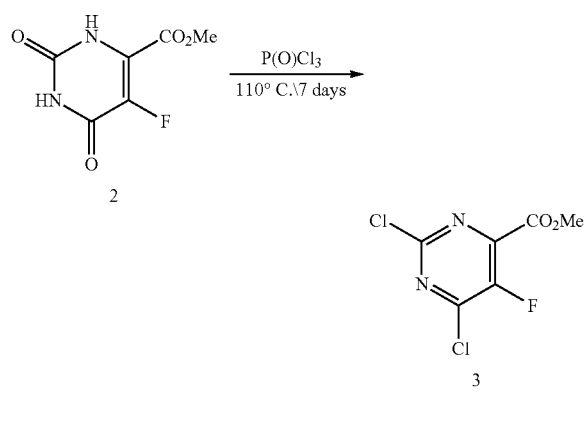

Compound 2 (46.0 g, 0.24 mol), N,N-dimethylformamide (0.5 mL), 1,4-dioxane (20 mL) were added to phosphorus oxychloride (700 mL) in sequence, and the system was stirred at 110° C. for 7 days. After LCMS detection showed the reaction completion, the system was vacuum concentrated, the obtained residue was slowly added dropwise to aqueous sodium bicarbonate solution and extracted with ethyl acetate (500 mL×3), the organic phases were dried over sodium sulfate and concentrated to give Compound 3 (53.7 g, yield >90%). Measured: ESI-MS m/z=225 [M+1]$^+$. $^1$H NMR (CDCl$_3$, 400 MHz): 3.94 (s, 3H).

1.3. Synthesis of Compound 4

Compound 4: methyl 2-chloro-5-fluoro-6-morpholinopyrimidine-4-carboxylate

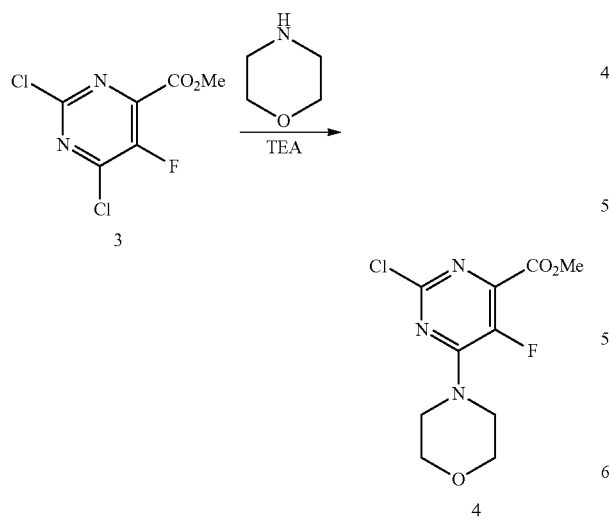

Compound 3 (53.7 g, 12.9 mmol) was dissolved in ethyl acetate (1.5 L), the reaction solution was cooled to 0° C., and then morpholine (44.6 g, 0.5 mol) was added in batches. The reaction was carried out at this temperature for 1 h. After LCMS detection showed the reaction completion, 100 mL of water was added, and the organic phase was dried over sodium sulfate and concentrated to give Compound 4 (60.0 g, yield=90%). Measured: ESI-MS m/z=276 [M+1]$^+$. $^1$H NMR (CDCl$_3$, 400 MHz): δ3.97 (s, 3H), 3.90-3.86 (m, 4H), 3.82-3.79 (m, 4H).

1.4. Synthesis of Compound 5

Compound 5: 2-chloro-5-fluoro-6-morpholinopyrimidine-4-carboxamide

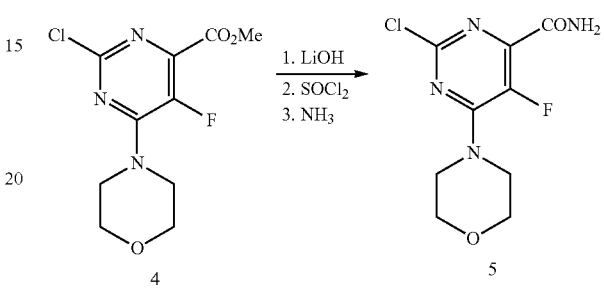

Compound 4 (55.0 g, 0.2 mol) was dissolved in methanol (250 mL), tetrahydrofuran (750 mL) and water (250 mL), and lithium hydroxide (12.6 g, 1.5 mol) was added in batches. The reaction solution was carried out at 0° C. for 1 h. After LCMS detection showed the reaction completion, aqueous hydrochloric acid solution (1 M) was added to adjust to pH=5, and the system was vacuum concentrated to give a crude product (50.0 g, yield >90%). The crude product (50 g, 0.19 mol) was dissolved in thionyl chloride (200 mL) and stirred at room temperature for 4 h. After LCMS detection showed the reaction completion, the system was vacuum concentrated to dryness, 1,4-dioxane (1 L) was added to prepare a solution, and then ammonia gas was continuously introduced, and the reaction solution was stirred at 0° C. for 4 h. After LCMS detection showed the reaction completion, the reaction solution was concentrated, ethyl acetate (500 mL) was added, the solid was filtered off, the filtrate was spin-dried, and purified by column chromatography (petroleum ether/ethyl acetate=1:1) to give Compound 5 (36.5 g, yield=71%). Measured: ESI-MS m/z=261 [M+1]$^+$. $^1$H NMR (DMSO-d6, 400 MHz): δ 8.01 (s, 1H) δ 7.85 (s, 1H), 3.76-3.71 (m, 4H), 3.70-3.68 (m, 4H).

1.5. Synthesis of Compound 6

Compound 6: 2-chloro-5-fluoro-6-morpholinopyrimidine-4-carbonitrile

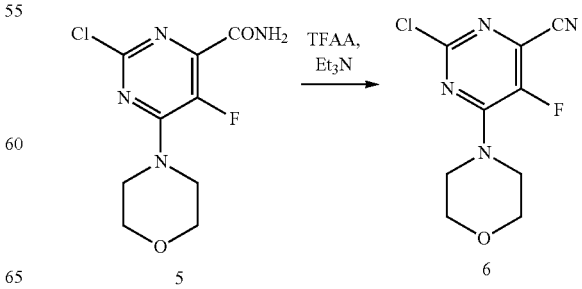

Compound 5 (36.5 g, 0.138 mol) was dissolved in dichloromethane (1.5 L), the reaction solution was cooled to 0° C., and then triethylamine (140 g, 1.38 mol) and trifluoroacetic anhydride (82 g, 0.69 mol) were added respectively. The system reacted at room temperature overnight. After LCMS detection showed the reaction completion, the reaction solution was concentrated, ethyl acetate was added, the organic phase was washed with sodium bicarbonate solution, saturated brine, dried over sodium sulfate and concentrated, and purified by column chromatography (petroleum ether/ethyl acetate=10:1) to give Compound 6 (25.0 g, yield=73%). Measured: ESI-MS m/z=243 [M+1]⁺. ¹H NMR (CDCl₃, 400 MHz): δ 3.90-3.88 (m, 4H), 3.84-3.80 (m, 4H).

1.6. Synthesis of Compound 8

Compound 8: 2-(4-isocyanatophenyl)-4,4,5,5-tetramethyl-1,3,2-dioxaborolane

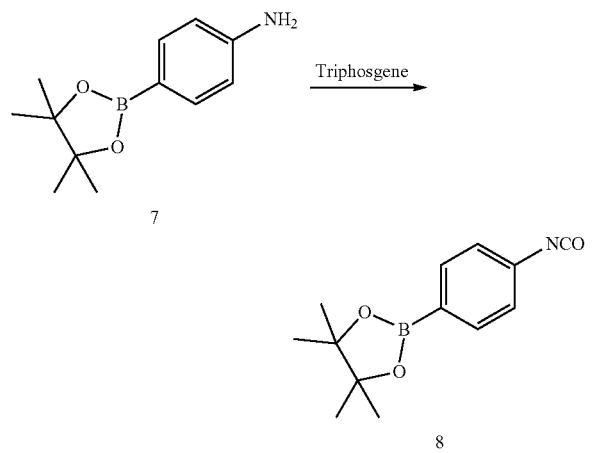

Compound 7 4-aminophenylboronic acid pinacol ester (10 g, 45.6 mmol) and triethylamine (13.8 g, 136.8 mmol) were added into 300 mL of dichloromethane, cooled to 0° C., triphosgene (8.1 g, 27.4 mmol) was slowly added at 0° C. in batches and then stirred at 0° C. for 50 minutes to give a solution of Compound 8, which was used directly in the next step.

1.7. Synthesis of Compound 9

Compound 9

1-(4-(hydroxymethyl)phenyl)-3-(4-(4,4,5,5-tetramethyl-1,3,2-dioxaborolan-2-yl)phenyl)urea

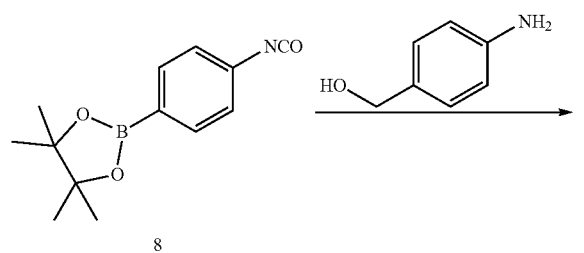

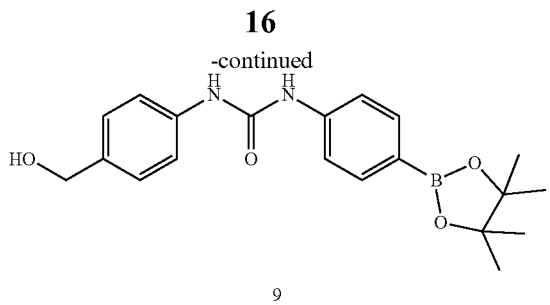

P-aminobenzyl alcohol (8.4 g, 68 mmol) was added to the above-mentioned solution of Compound 8 at 0° C., then the system was stirred at 0° C. for 15 minutes, warmed to room temperature, and stirred at room temperature for another 3 hours. After LC-MS detection showed the reaction completion, the reaction solution was concentrated and spin-dried, and extracted with dichloromethane, and the organic phase was washed with sodium bicarbonate solution and saturated sodium chloride solution, dried over anhydrous sodium sulfate, and filtered, and the filtrate was spin-dried, and purified by column chromatography (dichloromethane/methanol=40:1) to give a yellow solid, namely Compound 9 (11 g, yield=60%).

Measured: ESI-MS m/z=369 [M+1]⁺. ¹H NMR (DMSO-d6, 400 MHz): δ 9.02 (s, 1H), 8.89 (s, 1H), 7.60-7.58 (d, J=8 Hz, 2H), 7.49-7.47 (d, J=8.4 Hz, 2H), 7.42-7.40 (d, J=8 Hz, 2H), 7.24-7.21 (d, J=8.4 Hz, 2H), 5.06 (m, 1H), 4.44-4.42 (d, J=5.6 Hz, 2H), 1.28 (s, 12H).

1.8. Synthesis of Compound 10

Compound 10

1-(4-(4-cyano-5-fluoro-6-morpholinopyrimidin-2-yl)phenyl)-3-(4-(hydroxymethyl)phenyl)urea

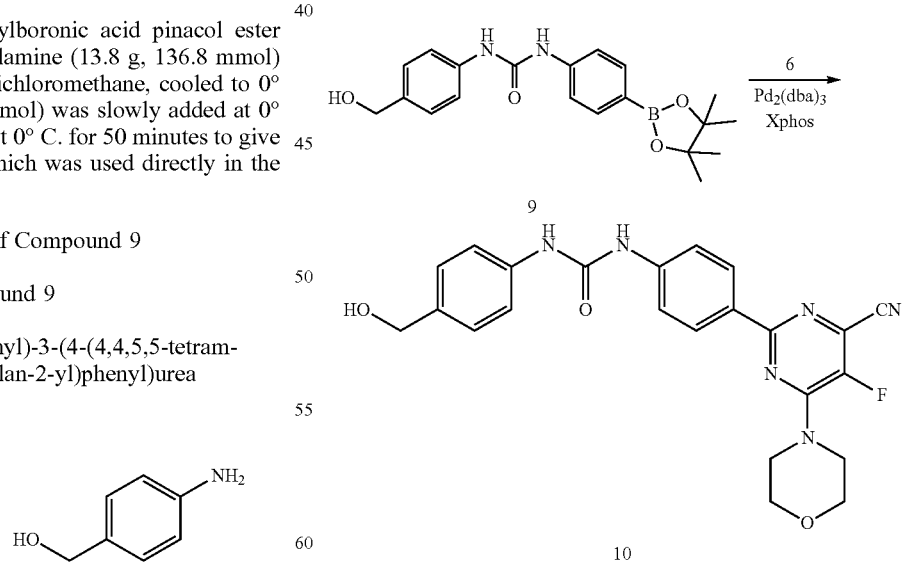

Compound 9 (3.5 g, 9.5 mmol) was dissolved in dioxane (100 mL) and water (5 mL), then Compound 6 (2.9 g, 12 mmol), sodium bicarbonate (2.4 g, 28.5 mmol), XPhos (400 mg) and Pd₂(dba)₃ (180 mg) were added, and the system was replaced with nitrogen for 3 times. Under the protection of nitrogen, the system was stirred at 85° C. for 2 days. The reaction solution was vacuum concentrated, ethyl acetate (20 mL) and water (30 mL) were added, stirred at room temperature for 0.5 hours, the system was filtered, and the filter cake was washed with water and ethyl acetate. The filter cake was added with ethyl acetate (15 mL) and stirred for another 0.5 hour, filtered, and vacuum dried to give Compound 10 (1.9 g, yield=44.7%). Measured: ESI-MS m/z=449 [M+1]$^+$. $^1$H NMR (DMSO-d6, 400 MHz): δ 8.98 (s, 1H), 8.72 (s, 1H), 8.17-8.15 (d, J=8.4 Hz, 2H), 7.58-7.56 (d, J=9.2 Hz, 2H), 7.43-7.41 (d, J=8 Hz, 2H), 7.24-7.22 (d, J=8 Hz, 2H), 5.08-5.05 (t, J=6 Hz, 1H), 4.44-4.42 (d, J=5.6 Hz, 2H), 3.87-3.86 (m, 4H), 3.77-3.75 (m, 4H).

1.9. Synthesis of Compound I-1

Compound I-1

1-(4-(3-amino-7-morpholino-1H-pyrazolo[4,3-d]pyrimidin-5-yl)phenyl)-3-(4-(hydroxymethyl)phenyl)urea

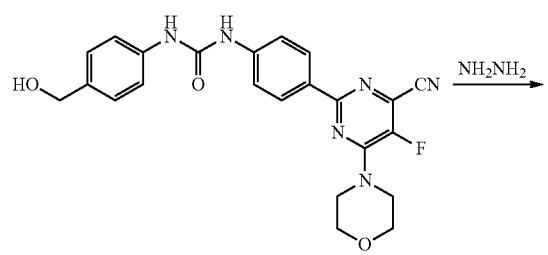

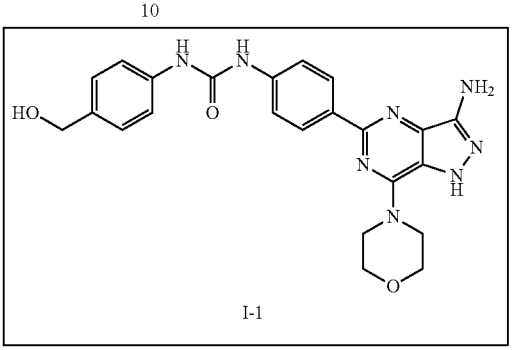

I-1

Compound 10 (0.9 g, 2.5 mmol) was suspended in 1,4-dioxane (80 mL), hydrazine hydrate (20 mL, 85%) was added, and stirred at 65° C. for 20 hours. After LCMS detection showed the reaction completion, 20 mL of water was added, the system was concentrated, precipitated a solid, filtered, and the filter cake was washed with water (10 mL×2), and purified by column chromatography (dichloromethane/methanol=20:1~5:1) to give Compound I-1 (0.55 g, yield=59.7%). Measured: $^1$H NMR (DMSO-d6+D$_2$O, 400 MHz): δ 8.29 (m, 2H), 7.54-7.52 (m, 2H), 7.44-7.41 (m, 2H), 7.26-7.214 (m, 2H), 4.44 (s, 2H), 4.28-3.79 (m, 8H). LCMS [mobile phase: from 85% water (0.02% NH$_4$Ac) and 15% CH$_3$CN to 40% water (0.02% NH$_4$Ac) and 60% CH$_3$CN in 15 min, finally under these conditions for 0.5 min.] purity is >96%, Rt=9.205 min; MS Calcd.: 460; MS Found: 461 [M+H]$^+$.

Embodiment 2: Preparation of Compound I-2

Compound I-2 was synthesized through the following route:

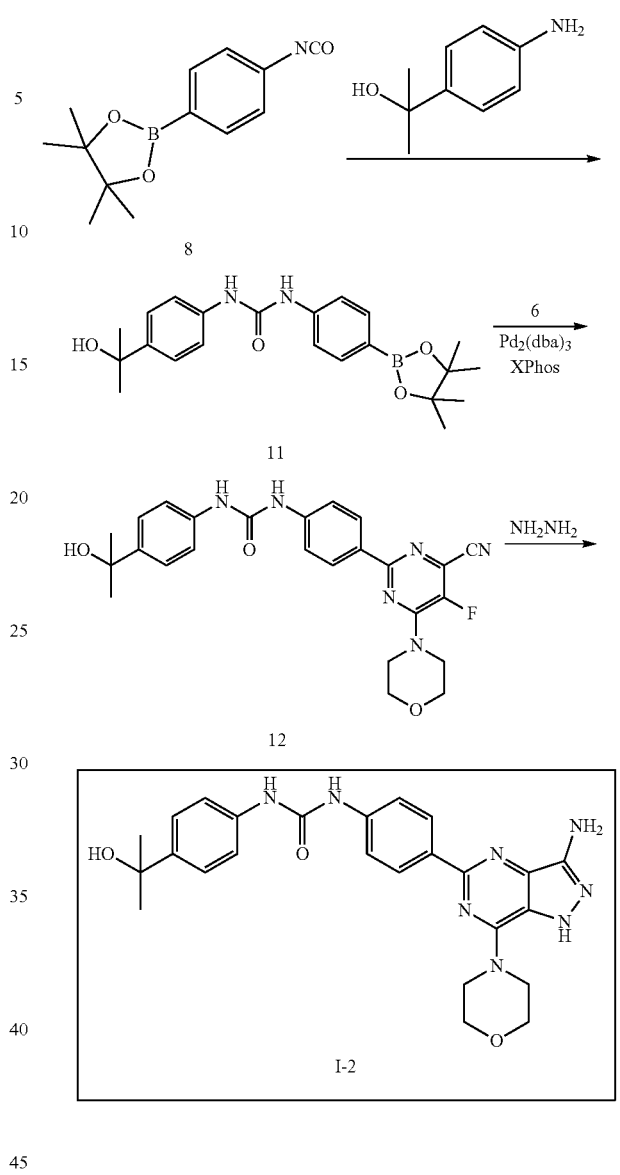

2.1. Synthesis of Compound 11

Compound 11

1-(4-(2-hydroxypropan-2-yl)phenyl)-3-(4-(4,4,5,5-tetramethyl-1,3,2-dioxaborolan-2-yl)phenyl)urea

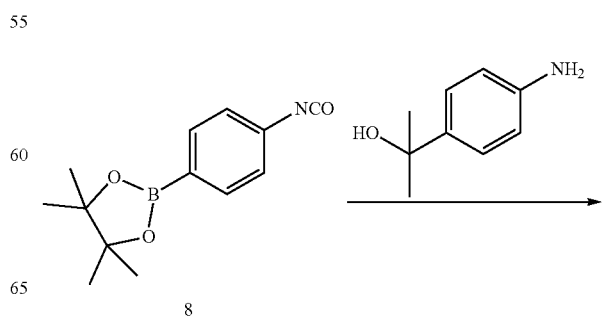

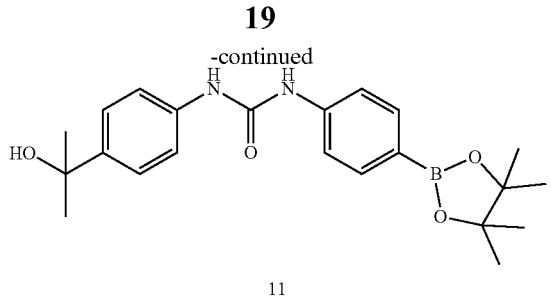

11

To a solution of Compound 8 (100 mL, from 4.34 g of Compound 7, 19.8 mmol) at 0° C. was added an amine

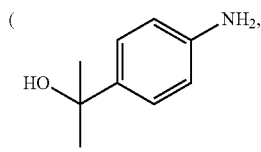

2.0 g, 13.2 mmol). The system was stirred at 0° C. for 15 minutes, naturally warmed to room temperature, and stirred at room temperature for another 4 hours. After LC-MS detection showed the reaction completion, the system was washed with saturated sodium chloride solution, the organic phase was dried over anhydrous sodium sulfate, filtered, and the filtrate was spin-dried to dryness, and diethyl ether (10 mL) was added to the residue, and the system was filtered and vacuum dried to give a white solid, namely Compound 11 (5.0 g, yield=96%). Measured: ESI-MS m/z=397 [M+1]$^+$ 2.2. Synthesis of Compound 12

Compound 12

1-(4-(4-cyano-5-fluoro-6-morpholinopyrimidin-2-yl)phenyl)-3-(4-(2-hydroxypropan-2-yl)phenyl)urea

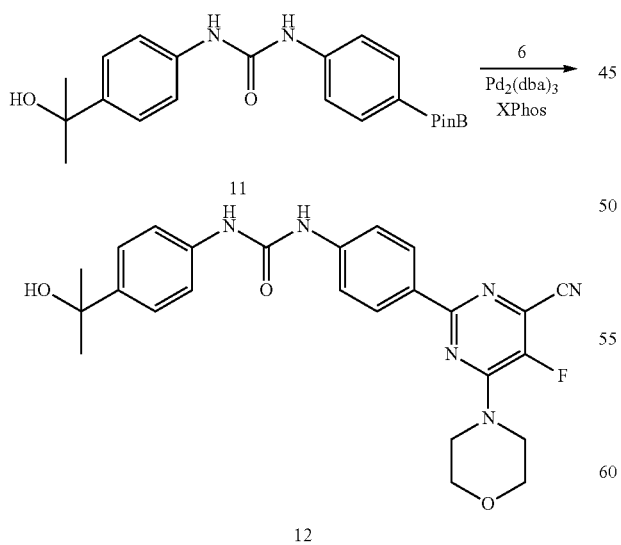

Compound 11 (2.0 g, 5 mmol) was dissolved in dioxane (40 mL) and water (4 mL), then Compound 6 (1.5 g, 6 mmol), sodium bicarbonate (1.3 g, 15 mmol), XPhos (400 mg) and Pd$_2$(dba)$_3$ (180 mg) were added, and the system was replaced with nitrogen for 3 times. Under the protection of nitrogen, the system was stirred at 90° C. for 16 hours. The reaction solution was vacuum concentrated, ethyl acetate (20 mL) and water (30 mL) were added, stirred at room temperature for 0.5 hours, the system was filtered, and the filter cake was washed with water and ethyl acetate. The filter cake was added with ethyl acetate (10 mL) and stirred for another 0.5 hour, filtered, and vacuum dried to give Compound 12 (1.2 g, yield=50%). Measured: ESI-MS m/z=477 [M+1]$^+$.

2.3. Synthesis of Compound I-2

Compound I-2

1-(4-(3-amino-7-morpholino-1H-pyrazolo[4,3-d]pyrimidin-5-yl)phenyl)-3-(4(2-hydroxypropan-2-yl)phenyl)urea

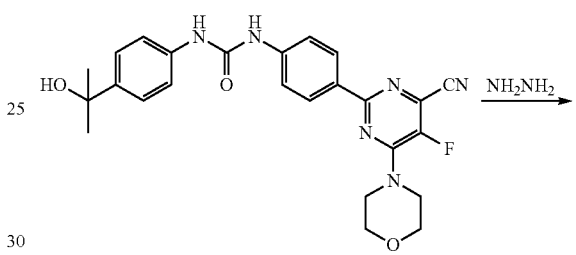

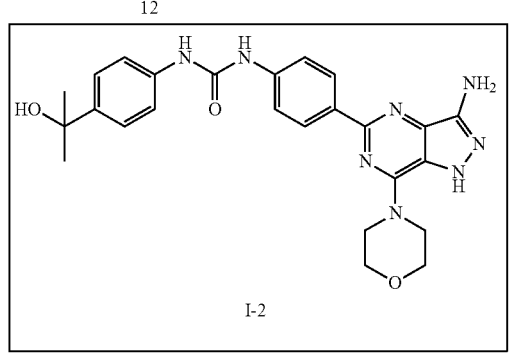

Compound 12 (2.0 g, 4.2 mmol) was suspended in dioxane (50 mL), hydrazine hydrate (10 mL, 85%) was added, and stirred at 70° C. for 16 h. After LCMS detection showed the reaction completion, 20 mL of water was added, the system was concentrated, precipitated a solid, filtered, and the filter cake was washed with water (10 mL×2), and purified by column chromatography (dichloromethane/methanol=20:1~5:1) to give Compound I-2 (1.0 g, yield=48.8%). Measured: $^1$H NMR (DMSO-d6, 400 MHz): δ 11.86 (1H), 8.79 (s, 1H), 8.62 (s, 1H), 8.31-8.29 (d, J=8.4 Hz, 2H), 7.57-7.53 (d, J=8.8 Hz, 2H), 7.37 (s, 4H), 5.43-5.40 (m, 1.5H), 4.90 (s, H), 3.97 (s, 3H), 3.78 (m, 8H), 1.41 (s, 6H). LCMS [mobile phase: from 80% water (0.02% NH$_4$Ac) and 20% CH$_3$CN to 50% water (0.02% NH$_4$Ac) and 50% CH$_3$CN in 6.5 min, finally under these conditions for 0.5 min.] purity is >95%, Rt=3.198 min; MS Calcd.: 488; MS Found: 489 [M+H]$^+$.

Embodiment 3: Preparation of Compound I-3

Compound I-3 was synthesized through the following route:

21

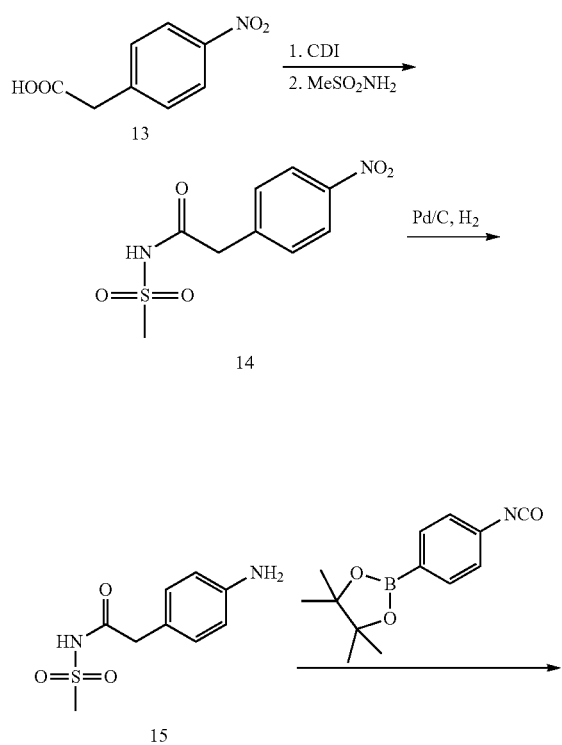

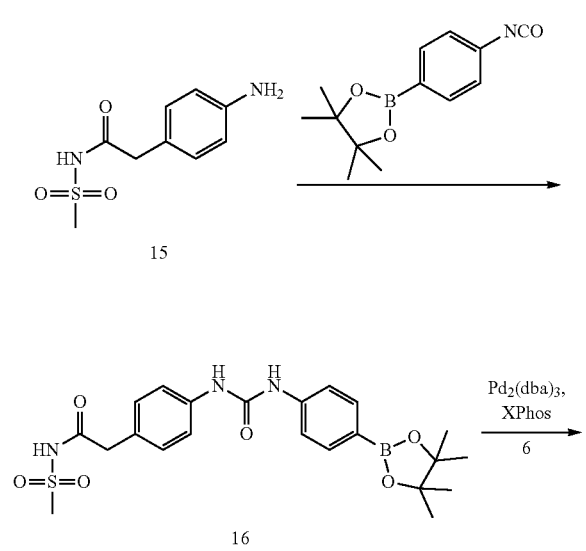

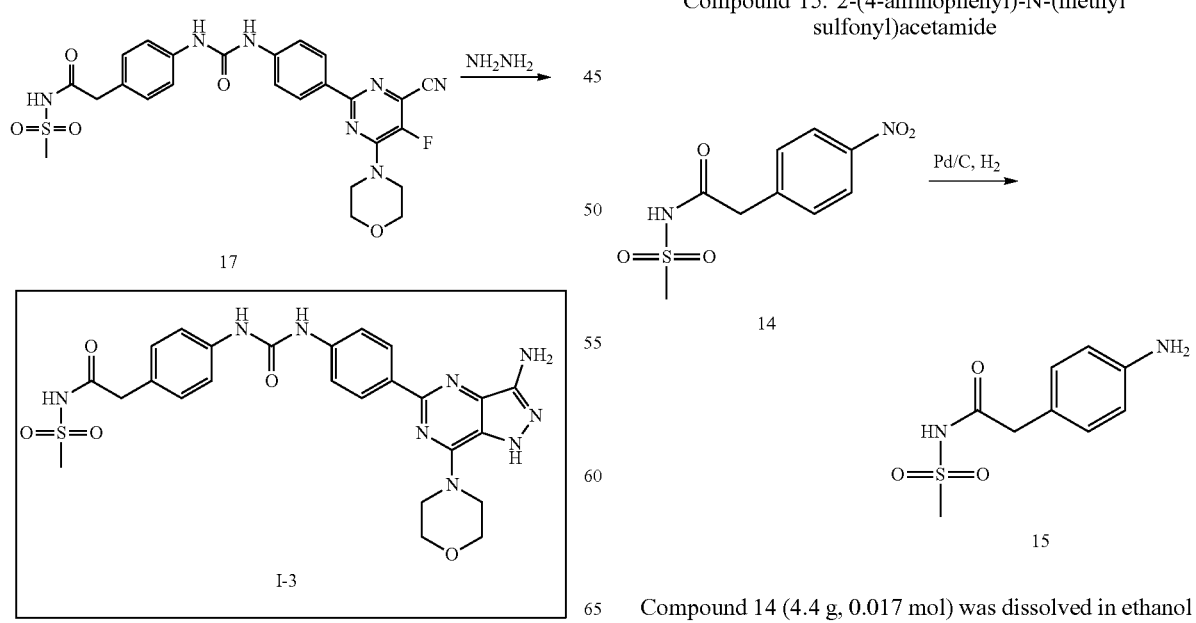

22

3.1. Synthesis of Compound 14

Compound 14: N-(methyl sulfonyl)-2-(4-nitrophenyl)acetamide

Compound 13 (6.0 g, 0.033 mol) was dissolved in dichloromethane (100 mL), CDI (10.7 g, 0.066 mol, N,N'-carbonyldiimidazole) was added, stirred at room temperature for 1 h, and methane sulfonamide (3.45 g, 0.036 mol) was added. The reaction solution was stirred at room temperature overnight, DBU (10.0 g, 0.066 mol) was added, and then stirred at room temperature overnight. The reaction solution was adjusted to pH=1 with hydrochloric acid (4N), the organic phase was washed with water, dried over anhydrous sodium sulfate, and filtered. The filtrate was vacuum concentrated, filtered, and the filter cake was washed with dichloromethane. The filter cake was vacuum dried to give a yellow solid, namely Compound 14 (4.4 g, yield=59.7%). Measured: ESI-MS m/z=257 [M−1]$^+$. $^1$H NMR (DMSO-d6, 400 MHz): δ 12.07 (s, 1H), 8.22-8.20 (d, J=8.8 Hz, 2H), 7.57-7.55 (d, J=8.4 Hz, 2H), 3.83 (s, 2H), 3.25 (s, 3H).

3.2. Synthesis of Compound 15

Compound 15: 2-(4-aminophenyl)-N-(methyl sulfonyl)acetamide

Compound 14 (4.4 g, 0.017 mol) was dissolved in ethanol (100 mL), concentrated hydrochloric acid (1.6 mL) and palladium on carbon (10%, 0.4 g) were added, and the system was replaced with hydrogen for 3 times. The reaction solution was stirred overnight at room temperature under hydrogen atmosphere. After LCMS monitored the reaction completion, the system was vacuum concentrated. Water (50 mL) was added to the residue and filtered off the palladium on carbon. The filtrate was vacuum spin-dried to dryness to give a white solid, namely Compound 15 (4.1 g, yield=91.7%). Measured: ESI-MS m/z=229 [M+1]$^+$. $^1$H NMR (DMSO-d6, 300 MHz): δ 7.38-7.33 (m, 4H), 3.70 (s, 2H), 3.26 (s, 3H).

3.3. Synthesis of Compound 16

Compound 16

N-(methylsulfonyl)-2-(4-(3-(4-(4,4,5,5-tetramethyl-1,3,2-dioxaborolan-2-yl)phenyl)ureido)phenyl)acetamide

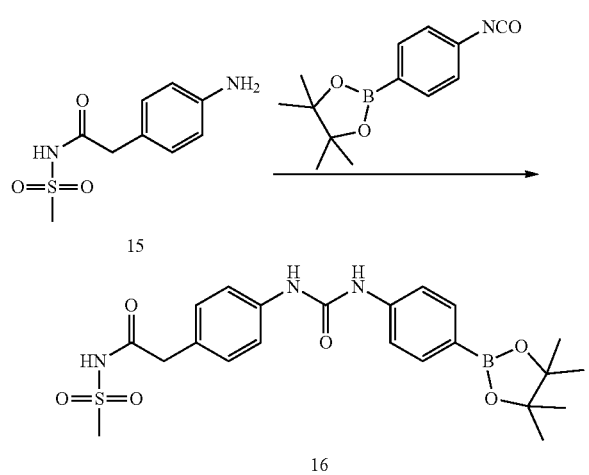

Compound 15 (6.3 g, 0.026 mol) was dissolved in dichloromethane (60 mL), triethylamine (5.9 mL, 0.044 mol) was added, and a solution of Compound 8 (100 mL, from 4.7 g of Compound 7, 17 mmol) was added in an ice-water bath, slowly warmed to room temperature, stirred overnight, extracted with water (30 mL×3), and the aqueous phase was acidified with hydrochloric acid (2N) to pH=6, filtered, and vacuum dried to give a crude white solid, namely Compound 16 (6.1 g, yield >76.2%). Measured: ESI-MS m/z=474 [M+1]$^+$ 3.4. Synthesis of Compound 17

Compound 17

2-(4-(3-(4-(4-cyano-5-fluoro-6-morpholinopyrimidin-2-yl)phenyl)ureido)phenyl)-N-(methylsulfonyl)acetamide

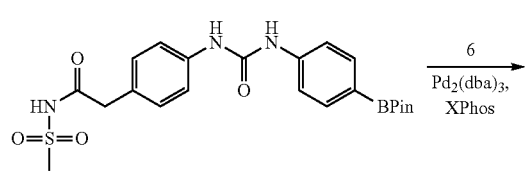

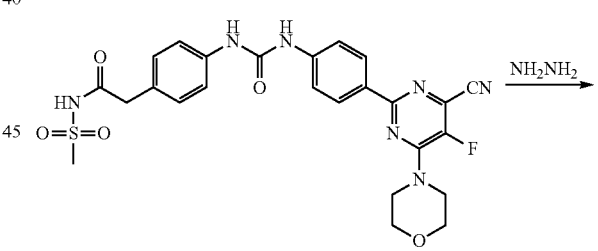

Compound 16 (5.0 g, 10.6 mmol) was dissolved in 1,4-dioxane (100 mL) and water (5 mL), then Compound 6 (2.6 g, 10.6 mmol), sodium bicarbonate (2.7 g, 31.8 mmol), XPhos (400 mg) and Pd$_2$(dba)$_3$ (180 mg) were added, and the system was replaced with nitrogen for 3 times. Under the protection of nitrogen, the system was stirred at 85° C. for 2 days. The reaction solution was vacuum concentrated, ethyl acetate (50 mL) and water (200 mL) were added, stirred at room temperature for 0.5 hours, the system was filtered, and the filter cake was washed with water and ethyl acetate. The aqueous phase was acidified with hydrochloric acid (2N) to pH=6, filtered, and the filter cake was stirred in ethyl acetate (15 mL) for 0.5 h, filtered, and vacuum dried to give a gray solid, namely Compound 17 (2.8 g, yield >47.8%). Measured: ESI-MS m/z=554 [M+1]$^+$ 3.5. Synthesis of Compound I-3

Compound I-3

2-(4-(3-(4-(3-amino-7-morpholino-1H-pyrazolo[4,3-d]pyrimidin-5-yl)phenyl)ureido)phenyl)-N-(methylsulfonyl)acetamide

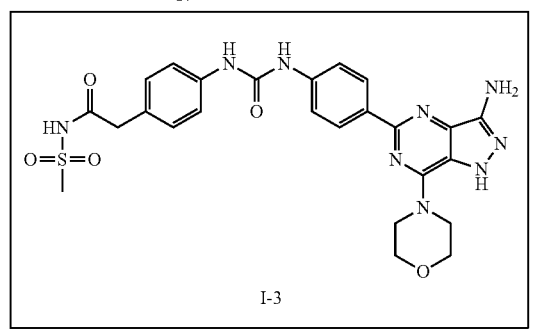

Compound 8 (2.0 g, 3.6 mmol) was suspended in dioxane (50 mL), hydrazine hydrate (20 mL, 85%) was added, and stirred at 65° C. for 15 min, and system was acidified in an ice-water bath with hydrochloric acid (2N) to pH=7, the system was filtered, and the filter cake was purified by silica gel column (DCM:MeOH=30:1~5:1) to give a yellow solid, which was further prepared by HPLC to give Compound I-3 (125 mg, yield=6.25%). Measured: ¹H NMR (DMSO-d6, 400 MHz): δ 11.90 (bs, 1H), 8.82 (s, 1H), 8.69 (s, 1H), 8.31-8.28 (d, J=8.4 Hz, 2H), 7.53-7.51 (d, J=8.4 Hz, 2H), 7.42-7.40 (d, J=8.4 Hz, 2H), 7.19-7.17 (d, J=8.8 Hz, 2H), 5.42 (bs, 2H), 3.97 (m, 4H), 3.79 (m, 4H), 3.49 (s, 2H), 3.14 (s, 3H). LCMS [mobile phase: from 90% water (0.02% NH₄Ac) and 10% CH₃CN to 50% water (0.02% NH₄Ac) and 50% CH₃CN in 6.5 min, finally under these conditions for 0.5 min.] purity is >95%, Rt=2.992 min; MS Calcd.: 565; MS Found: 566 [M+H]⁺.

Embodiment 4: Preparation of Compound I-4

Compound I-4 was synthesized through the following route:

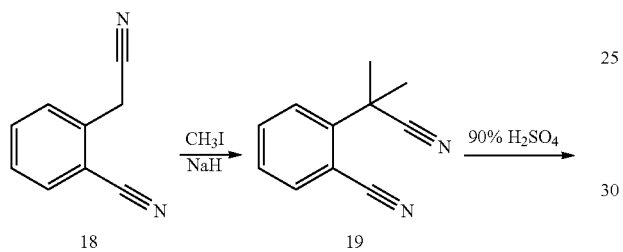

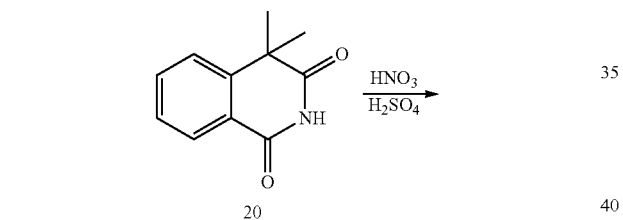

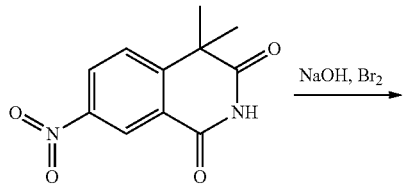

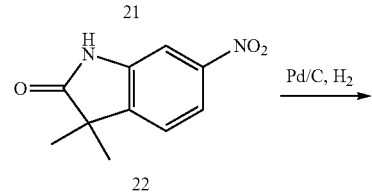

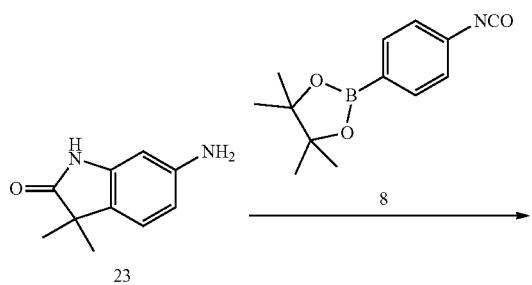

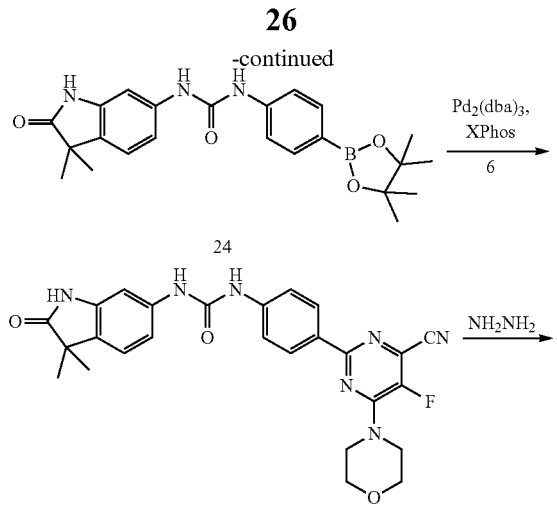

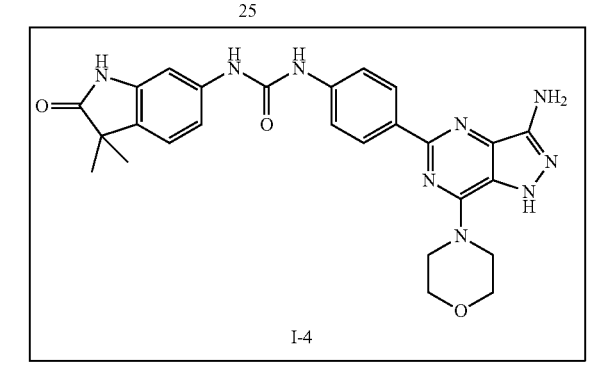

I-4

4.1. Synthesis of Compound 19

Compound 19: 2-(2-cyanopropan-2-yl)benzonitrile

Sodium hydride (60%, 12.0 g, 0.3 mol) was added to tetrahydrofuran (150 mL), cooled to 0° C. in an ice-water bath, a solution of Compound 18 (14.2 g, 0.1 mol) in tetrahydrofuran (50 mL) was added dropwise, after addition, the system was stirred at room temperature for 1 hour. The reaction solution was cooled to 0° C., CH₃I (57.0 g, 0.4 mol) was added dropwise, stirred overnight at room temperature, poured into ice water (200 mL) to quench, extracted with ethyl acetate (50 mL×2), and the organic phase was dried over sodium sulfate and concentrated, then methyl tert-butyl ether (20 mL) and petroleum ether (50 mL) were added, stirred and filtered, and vacuum dried to give a yellow solid, namely Compound 19 (13.8 g, yield 18.1%). Measured: ¹H NMR (CDCl₃, 400 MHz): δ 7.79-7.76 (m, 2H), 7.67-7.62 (m, 1H), 7.48-7.44 (m, 1H), 1.97 (s, 6H).

4.2. Synthesis of Compound 20

Compound 20:
4,4-dimethylisoquinoline-1,3(2H,4H)-dione

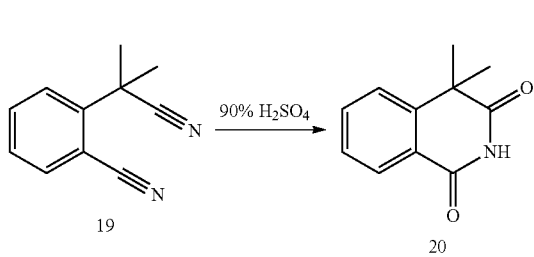

In an ice-water bath, Compound 19 (13.8 g, 0.081 mol) was added to H$_2$SO$_4$ (90%, 44 mL), stirred at room temperature for 2 days, and then stirred at 60° C. overnight. The reaction solution was cooled to room temperature and then poured into stirring ice water, filtered, washed with water, and vacuum dried to give an off-white solid, namely Compound 20 (14.9 g, yield 97.3%). Measured: ESI-MS m/z=188 [M−1]$^-$. $^1$H NMR (CDCl$_3$, 400 MHz): 8.41 (bs, 1H), 8.24-8.22 (m, 1H), 7.70-7.66 (m, 1H), 7.51-7.44 (m, 2H), 1.66 (s, 6H).

4.3. Synthesis of Compound 21

Compound 21:
4,4-dimethyl-7-nitroisoquinoline-1,3(2H,4H)-dione

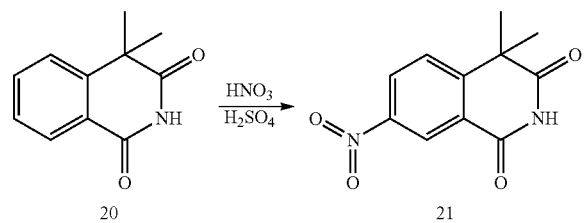

Fuming nitric acid (60 mL) was cooled to 0° C., concentrated sulfuric acid (60 mL) was slowly added, and then Compound 20 (14.0 g, 0.074 mol) was added in batches to give a yellow solution. The solution was stirred at 0~5° C. for 2 hours, and then poured into stirring ice water (400 mL), filtered, washed with water, and vacuum dried to give an off-white solid, namely Compound 21 (17 g, yield 98.2%). Measured: ESI-MS m/z=233 [M−1]$^-$. $^1$H NMR (acetone-d6, 400 MHz): δ 10.44 (bs, 1H), 8.89-8.86 (d, J=2.8 Hz, 1H), 8.58-8.55 (m, 1H), 8.10-8.08 (d, J=8.4 Hz, 1H), 1.76 (s, 6H).

4.4. Synthesis of Compound 22

Compound 22: 3,3-dimethyl-6-nitroindolin-2-one

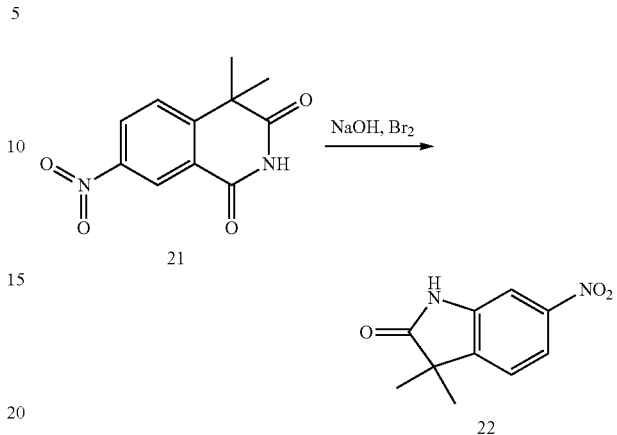

NaOH (19.6 g, 0.49 mol) was dissolved in water (300 mL), cooled to below 5° C. in an ice-water bath, Br$_2$ (20.7 g, 0.13 mol) was added in batches, stirred for 10 minutes, and then Compound 21 (19.0 g, 0.081 mol) was added and stirred overnight at room temperature. NaOH (10.0 g, 0.25 mol) and water (40 mL) were added to the reaction solution. The reaction solution was stirred at 80° C. for 0.5 hours and then cooled to room temperature. In an ice-water bath, the pH was adjusted to 1 with concentrated hydrochloric acid, and the system was filtered, washed with water, and vacuum dried to give a yellow solid, namely Compound 22 (10.0 g, yield 59.9%). Measured: ESI-MS m/z=205 [M−1]$^-$. $^1$H NMR (CDCl$_3$, 400 MHz): δ 9.00 (s, 1H), 8.00-7.97 (m, 1H), 7.79-7.78 (d, J=2.4 Hz, 1H), 7.35-7.33 (d, J=7.6 Hz, 1H), 1.45 (s, 6H).

4.5. Synthesis of Compound 23

Compound 23: 6-amino-3,3-dimethylindolin-2-one

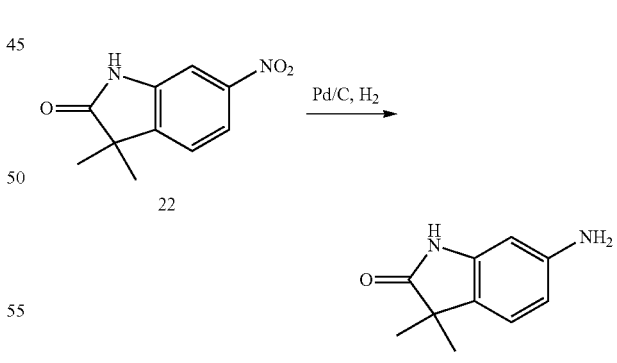

Compound 22 (10.0 g, 0.19 mol) was dissolved in ethanol (700 mL) and dichloromethane (150 mL), concentrated hydrochloric acid (10 mL) and palladium on carbon (10%, 400 mg) were added, and the system was replaced with hydrogen for 3 times, and stirred at room temperature overnight. The palladium carbon was filtered off, the filtrate was vacuum concentrated, the residue was added with methyl tert-butyl ether, filtered, and vacuum dried to give a yellow solid, namely Compound 23 (9.0 g, yield=87.3%). Measured: ESI-MS m/z=177 [M+1]⁺. ¹H NMR (CDCl₃, 400 MHz): δ 10.48 (s, 1H), 7.31-7.29 (d, J=7.6 Hz, 1H), 6.83-6.79 (m, 2H), 1.22 (s, 6H).

4.6. Synthesis of Compound 24

Compound 24

1-(3,3-dimethyl-2-oxoindolin-6-yl)-3-(4-(4,4,5,5-tetramethyl-1,3,2-dioxaborolan-2-yl)phenyl)urea

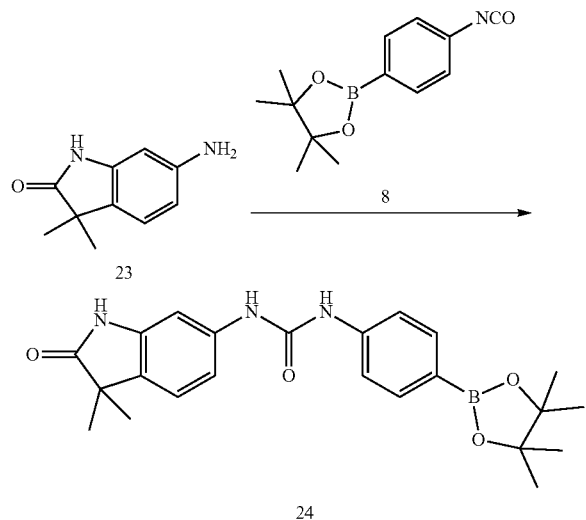

To a solution of Compound 8 (100 mL, from 5.3 g of Compound 7, 23.7 mmol) was added dropwise a dichloromethane solution of Compound 23 (4.0 g, 18.8 mmol) and triethylamine (2.6 mL, 18.8 mmol) at 0 to 5° C. The reaction solution was stirred overnight at room temperature, washed with aqueous sodium bicarbonate solution, washed with water, and the organic phase was vacuum concentrated, filtered, and the filter cake was washed with a small amount of dichloromethane, and vacuum dried to give an off-white solid, namely Compound 24 (5.2 g, yield 65.7%). Measured: ESI-MS m/z=295 [M+1]⁺

4.7. Synthesis of Compound 25

Compound 25

1-(4-(4-cyano-5-fluoro-6-morpholinopyrimidin-2-yl)phenyl)-3-(4-(hydroxymethyl)phenyl)urea

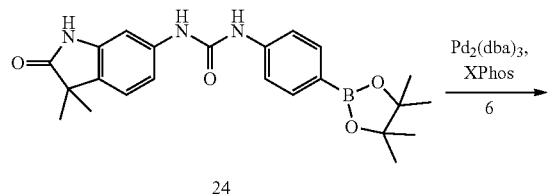

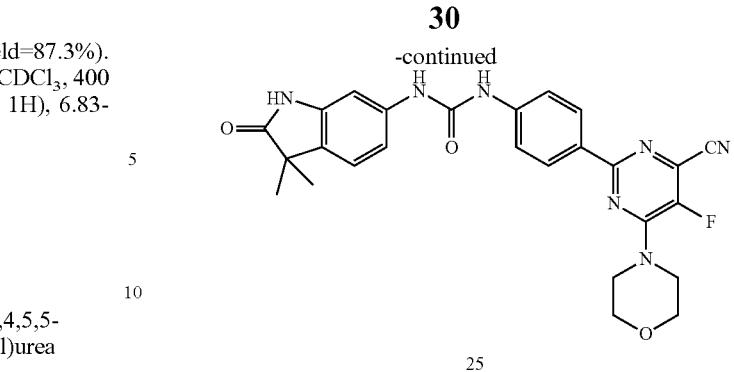

Compound 24 (2.0 g, 4.7 mmol) was dissolved in 1,4-dioxane (25 mL) and water (1.25 mL), then Compound 6 (1.1 g, 4.7 mmol), sodium bicarbonate (1.2 g, 14.2 mmol), XPhos (600 mg) and Pd₂(dba)₃ (300 mg) were added. The reaction solution was stirred at 90° C. overnight. After LCMS detection showed the reaction completion, 10 mL of water was added, and the system was extracted with ethyl acetate, and the organic phase was dried over anhydrous sodium sulfate, and filtered, and the filtrate was vacuum concentrated, and purified by column chromatography (dichloromethane/methanol=20:1) to give Compound 25 (500 mg, yield=20%). Measured: ESI-MS m/z=502 [M+1]⁺. ¹H NMR (DMSO-d6, 400 MHz): δ 10.28 (s, 1H), 8.92 (s, 1H), 8.74 (s, 1H), 8.17-8.15 (d, J=7.2 Hz, 1H), 7.58-7.56 (d, J=8 Hz, 2H), 7.27 (s, 1H), 7.17-7.15 (d, J=8 Hz, 1H), 6.88-6.84 (m, 1H).

4.8. Synthesis of Compound I-4

Compound I-4

1-(4-(3-amino-7-morpholino-1H-pyrazolo[4,3-d]pyrimidin-5-yl)phenyl)-3-(3,3-dimethyl-2-oxoindolin-6-yl)urea

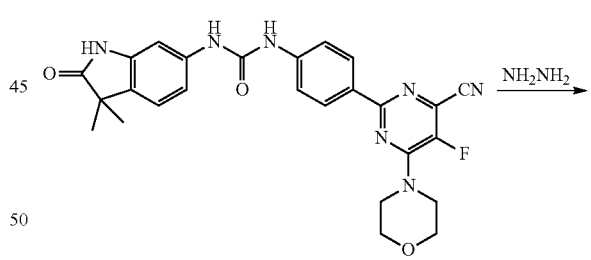

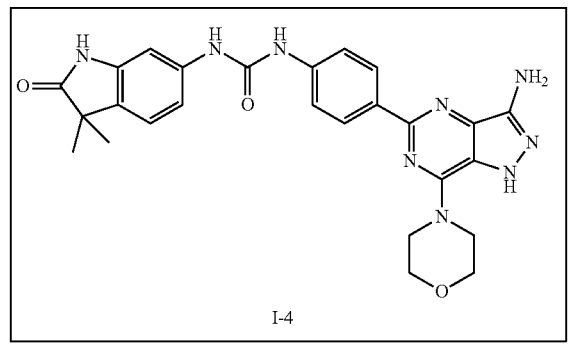

Compound 25 (1.26 g, 2.5 mmol) was dissolved in 1,4-dioxane (80 mL), hydrazine hydrate (25 mL, 85%) was added, and stirred at 70° C. for 20 h. After LCMS detection showed the reaction completion, 10 mL of water was added, the system was concentrated, precipitated a solid, filtered, and the filter cake was washed with water (10 mL×2), and purified by column chromatography (dichloromethane/methanol=20:1~5:1) to give Compound I-4 (0.86 g, yield=47%). Measured: $^1$H NMR (DMSO-d6, 400 MHz): δ 12.84 (s, 0.3H), 11.85 (s, 0.6H), 10.28 (s, 1H), 8.88-8.70 (m, 2H), 8.301 (s, 2H), 7.53-7.51 (d, J=8 Hz, 2H), 7.30 (s, 1H), 7.16-7.14 (d, J=8 Hz, 1H), 6.86-6.83 (d, J=8 Hz, 1H), 5.70 (s, 0.6H), 5.28 (s, 1H), 4.34-4.16 (m, 1H), 4.10-3.78 (m, 7H), 3.18-3.17 (d, J=4 Hz, 1H), 1.23 (s, 6H). LCMS [mobile phase: from 80% water (0.02% NH$_4$Ac) and 20% CH$_3$CN to 30% water (0.02% NH$_4$Ac) and 70% CH$_3$CN in 6.5 min, finally under these conditions for 0.5 min.] purity is >96%, Rt=2.888 min; MS Calcd.: 513; MS Found: 514 [M+H]$^+$.

Embodiment 5: Preparation of Compound I-5

Compound I-5 was synthesized through the following route:

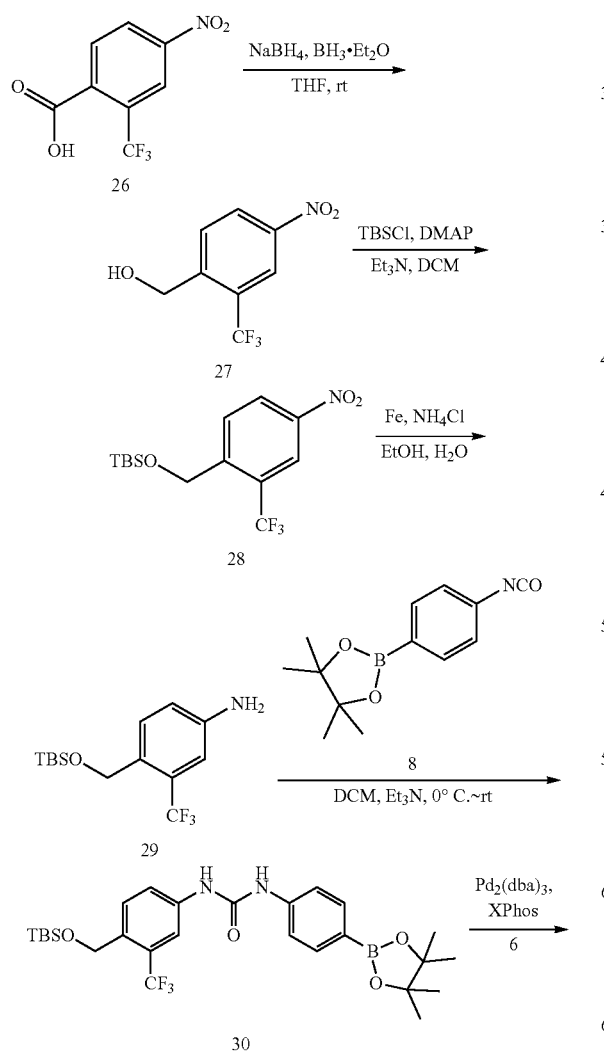

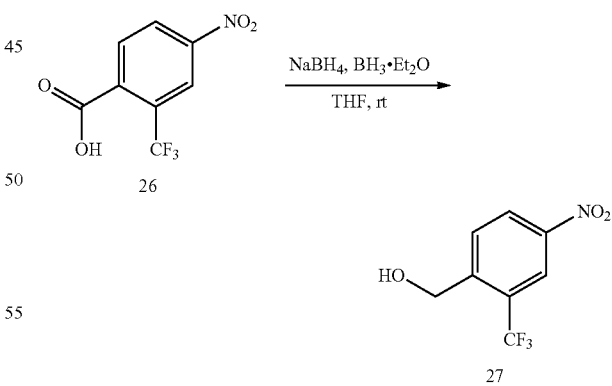

5.1. Synthesis of Compound 27

Compound 27:
(4-nitro-2-(trifluoromethyl)phenyl)methanol

Compound 26 (25.0 g, 106.4 mmol) was dissolved in tetrahydrofuran (100 mL), sodium borohydride (11.5 g, 319.1 mmol) was slowly added in an ice bath, and boron trifluoride diethyl etherate (20 mL) was slowly added dropwise, and stirred at room temperature overnight. After TLC detection showed the reaction completion, 100 mL of brine was added, and the system was extracted with ethyl acetate (300 mL×3), and the organic phases were dried over sodium sulfate and concentrated to give Compound 27 (14.5 g, yield=61%). Measured: ESI-MS m/z=222 [M+1]+

5.2. Synthesis of Compound 28

Compound 28: tert-butyldimethyl((4-nitro-2-(trifluoromethyl)benzyl)oxy)silane

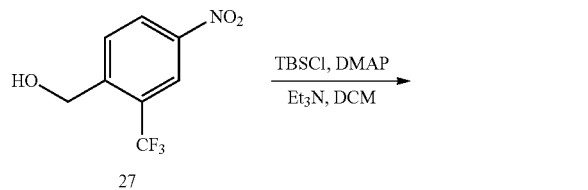

Compound 27 (14.0 g, 63.64 mmol), tert-butyldimethylsilyl chloride (19.2 g, 127.27 mmol), triethylamine (16.1 g, 159.1 mmol) and p-dimethylaminopyridine (0.78 g, 6.36 mmol) were added to dichloromethane (120 mL) in ice bath, and then the reaction solution was stirred at room temperature for 2 h. After TLC detection showed the reaction completion, 100 mL of brine was added, and the system was extracted with dichloromethane (200 mL×3), and the organic phases were dried over sodium sulfate and purified by column chromatography (petroleum ether/ethyl acetate=100:1-50:1) to give Compound 28 (15.0 g, yield=70%), which was directly used in the next step.

5.3. Synthesis of Compound 29

Compound 29: 4-(((tert-butyldimethylsilyl)oxy)methyl)-3-(trifluoromethyl)aniline

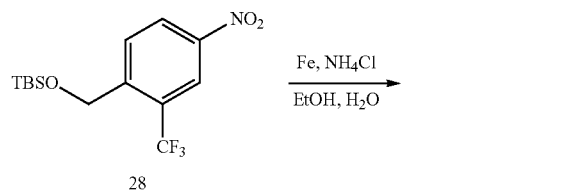

Compound 28 (15.0 g, 44.78 mmol) was dissolved in ethanol/water (200 mL/80 mL), ammonium chloride (15.0 g, 268.68 mmol) was added, and the system was warmed to a temperature of 80° C., then iron powder (11.0 g, 201.49 mmol) was added, the reaction was carried out at this temperature for 1 h. After LCMS detection showed the reaction completion, brine (100 mL) was added, and the system was filtered. And the filtrate was extracted with ethyl acetate (200 mL×3), and the organic phases were dried over sodium sulfate and concentrated to give Compound 29 (11.0 g, yield=80%). Measured: ESI-MS m/z=306 [M+1]+. $^1$H NMR (CDCl$_3$, 400 MHz): δ 7.49 (d, J=8.0 Hz, 1H), 6.90 (s, 1H), 6.83 (d, J=8.0 Hz, 1H), 4.78 (s, 2H), 0.94 (s, 9H), 0.09 (s, 6H).

5.4. Synthesis of Compound 30

Compound 30

1-(4-(((tert-butyldimethylsilyl)oxy)methyl)-3-(trifluoromethyl)phenyl)-3-(4-(4,4,5,5-tetramethyl-1,3,2-dioxaborolan-2-yl)phenyl)urea

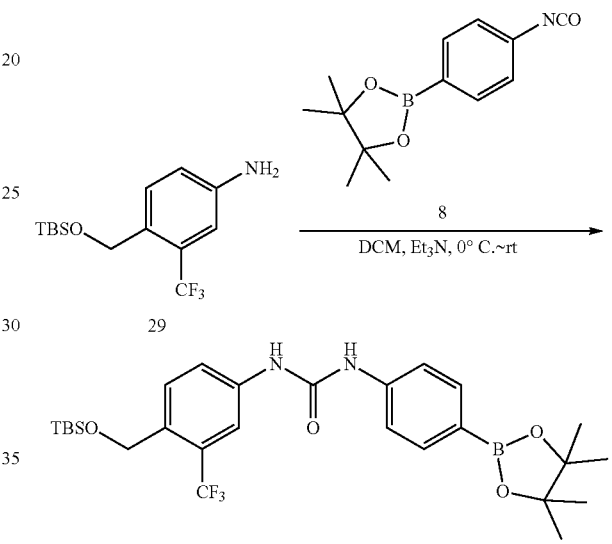

Compound 29 (6.0 g, 19.68 mol) was dissolved in tetrahydrofuran (90 mL), and then Compound 8 (12.0 g, 49.19 mmol) was added. The system reacted at room temperature overnight. After LCMS detection showed the reaction completion, the reaction solution was vacuum concentrated, and purified by column chromatography (petroleum ether/ethyl acetate=10:1-5:1) to give Compound 30 (5.5 g, yield=50%). Measured: ESI-MS m/z=551.6 [M+1]+

5.5. Synthesis of Compound 31

Compound 31

1-(4-(((tert-butyldimethylsilyl)oxy)methyl)-3-(trifluoromethyl)phenyl)-3-(4-(4-cyano-5-fluoro-6-morpholinopyrimidin-2-yl)phenyl)urea

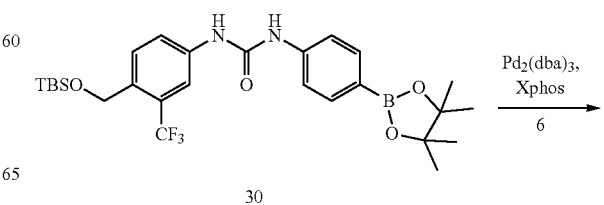

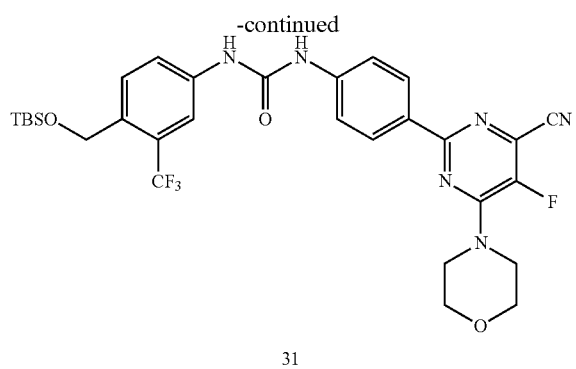

31

Compound 30 (6.5 g, 11.82 mmol) was dissolved in dioxane (50 mL)/water (5 mL), then Compound 6 (3.2 g, 13.00 mmol), sodium bicarbonate (3.0 g, 35.46 mmol), XPhos (563 mg, 1.19 mmol) and Pd$_2$(dba)$_3$ (220 mg, 0.24 mmol) were added. The reaction was carried out at 85° C. overnight. After LCMS detection showed the reaction completion, 35 mL of brine was added, and the system was extracted with ethyl acetate, the organic phase was dried over sodium sulfate, concentrated, and purified by column chromatography (petroleum ether/ethyl acetate=3:1-1:2) to give Compound 31 (3.0 g, yield=40%). Measured: ESI-MS m/z=629.7 [M−1]$^-$.

5.6. Synthesis of Compound 32

Compound 32

1-(4-(3-amino-7-morpholino-1H-pyrazolo[4,3-d]pyrimidin-5-yl)phenyl)-3-(4-(((tert-butyldimethylsilyl)oxy)methyl)-3-(trifluoromethyl)phenyl)urea

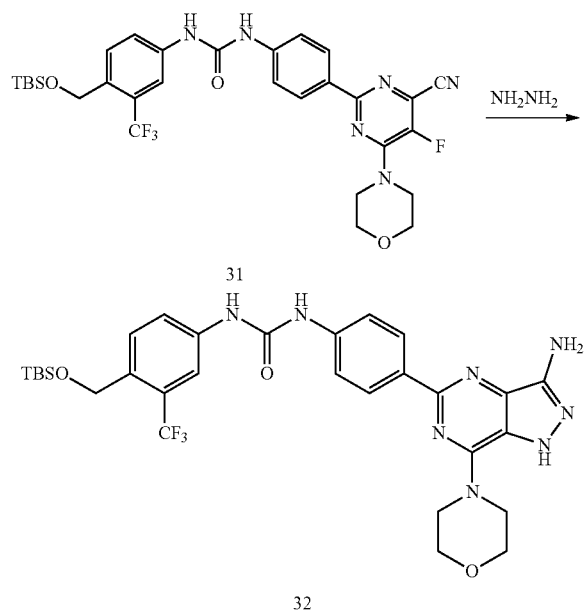

Compound 31 (2.8 g, 4.45 mmol) was dissolved in 1,4-dioxane (50 mL), and then hydrazine hydrate (12 mL, 85%) was added. The reaction was carried out at 70° C. for 2 days. After LCMS detection showed the reaction completion, 35 mL of brine was added, and the system was extracted with ethyl acetate, the organic phase was dried over sodium sulfate, concentrated, purified by silica gel column (dichloromethane/methanol=100:1-10:1), and then purified by reversed-phase column to give Compound 32 (1.30 g, yield=45%). Measured: ESI-MS m/z=643.7 [M+1]$^+$. $^1$H NMR (DMSO-d6, 400 MHz): δ 9.02 (s, 1H), 8.89 (s, 1H), 8.21 (d, J=8.0 Hz, 2H), 7.92 (s, 1H), 7.52 (brs, 2H), 7.44 (d, J=8.0 Hz, 2H), 4.69 (s, 2H), 3.78-3.50 (m, 8H), 0.81 (s, 9H), 0.00 (s, 6H).

5.7. Synthesis of Compound I-5

Compound I-5

1-(4-(3-amino-7-morpholino-1H-pyrazolo[4,3-d]pyrimidin-5-yl)phenyl)-3-(4-(hydroxymethyl)-3-(trifluoromethyl)phenyl)urea

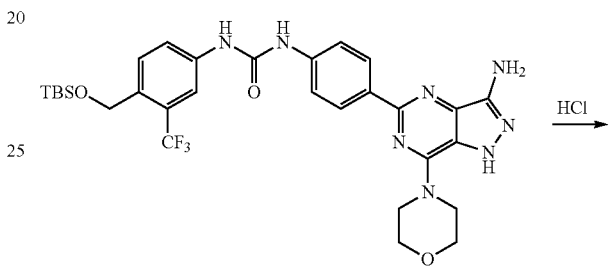

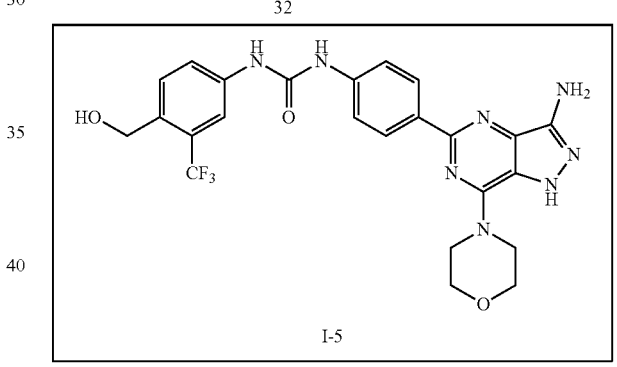

Compound 32 (1.3 g, 2.02 mmol) was dissolved in 0.5M of 1,4-dioxane (20 mL), and then water (3 mL) was added. The system was stirred at room temperature for 2 h, and after LCMS detection showed the reaction completion, the system was filtered. The obtained insolubles were respectively slurried with acetonitrile, ethyl acetate and methyl tert-butyl ether, and dried to give Compound I-5 (0.85 g, yield 80%). Measured: $^1$H NMR (DMSO-d6, 400 MHz): δ 9.67 (s, 1H), 9.57 (s, 1H), 8.37 (d, J=8.4 Hz, 2H), 7.95 (s, 1H), 7.69-7.62 (m, 4H), 4.61 (s, 2H), 4.45-4.15 (m, 4H), 3.84-3.78 (m, 4H). $^1$H NMR (DMSO-d6+D$_2$O, 400 MHz): δ 9.60 (s, 0.3H), 9.48 (s, 0.3H), 8.33 (d, J=8.4 Hz, 2H), 7.97 (s, 1H), 7.72-7.64 (m, 4H), 4.64 (s, 2H), 4.46-4.24 (m, 4H), 3.87 (brs, 4H). LCMS [mobile phase: from 80% water (0.02% NH$_4$Ac) and 20% CH$_3$CN to 30% water (0.02% NH$_4$Ac) and 70% CH$_3$CN in 6.5 min, finally under these conditions for 0.5 min.] purity is >95%, Rt=2.974 min; MS Calcd.: 528; MS Found: 529 [M+H]$^+$.

Embodiment 6: Preparation of Compound I-6

Compound I-6 was synthesized through the following route:

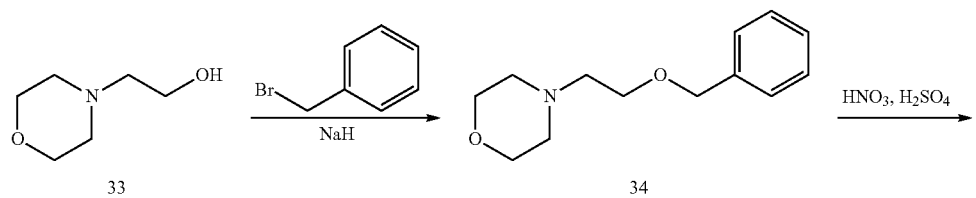
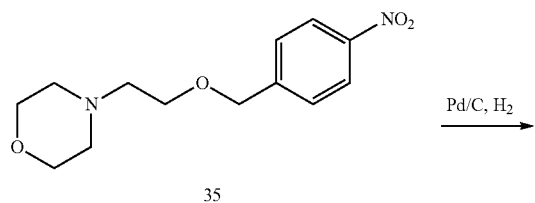
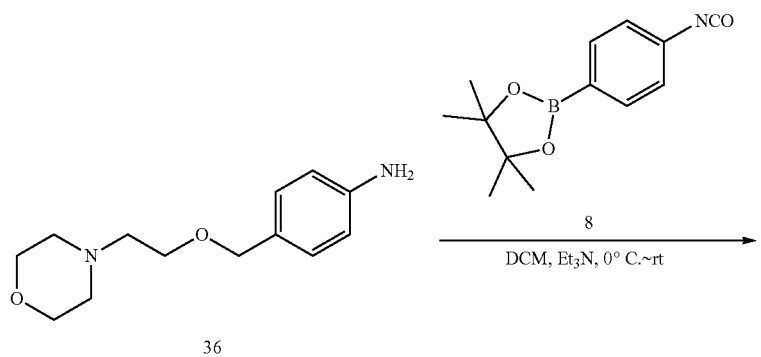
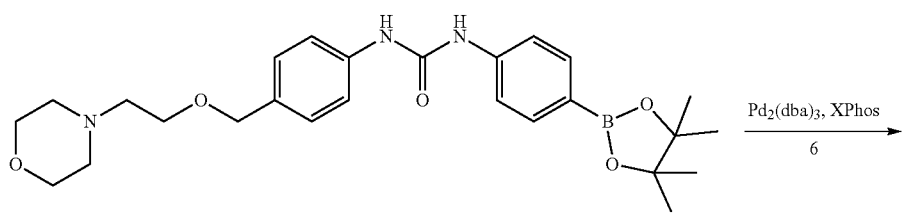
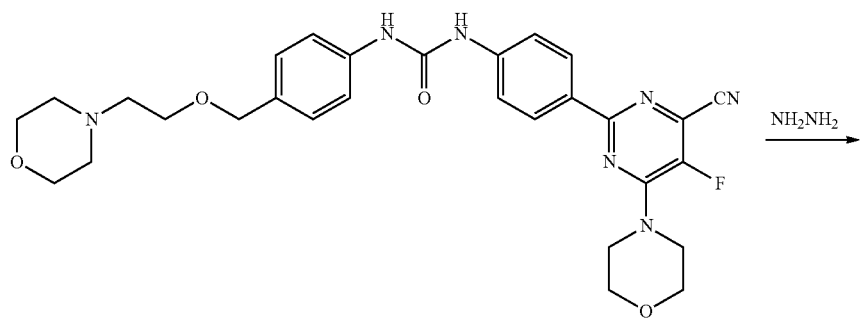

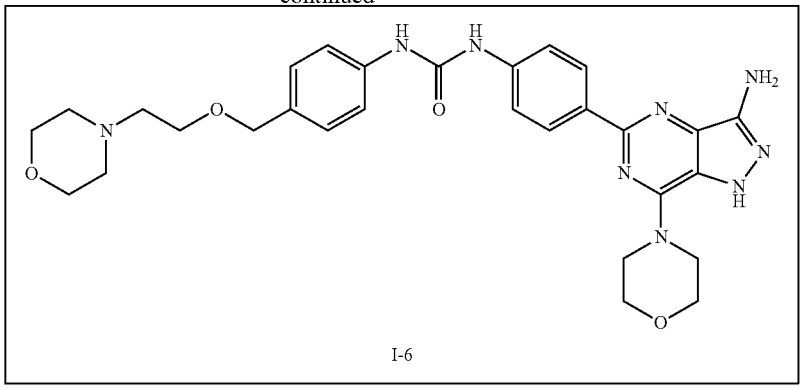

I-6

6.1. Synthesis of Compound 34

Compound 34: 4-(2-(benzyloxy)ethyl)morpholine

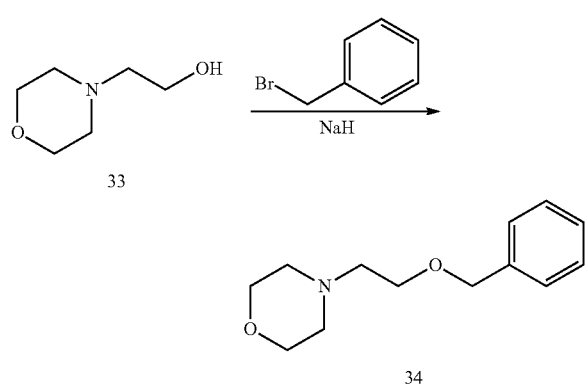

Compound 33 (32.8 g, 0.25 mol) was dissolved in DMF (200 mL), NaH (10 g, 0.25 mol) was added in batches in an ice-water bath, and the system was stirred at room temperature for 1.5 hours, and then benzyl bromide (39.3 g, 0.23 mol) was added dropwise The reaction solution was stirred at room temperature for 16 hours, vacuum concentrated, then ethyl acetate (100 mL) was added and the reaction solution was washed with water and saturated brine. The organic phase was vacuum concentrated, and purified by silica gel column (DCM:MeOH=10:1) to give a colorless oil, namely Compound 34 (40 g, yield 78%). Measured: ESI-MS m/z=222 [M+1]$^+$

6.2. Synthesis of Compound 35

Compound 35: 4-(2-((4-nitrobenzyl)oxy)ethyl)morpholine

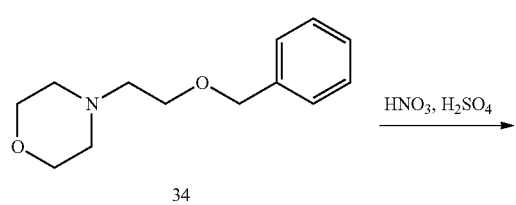

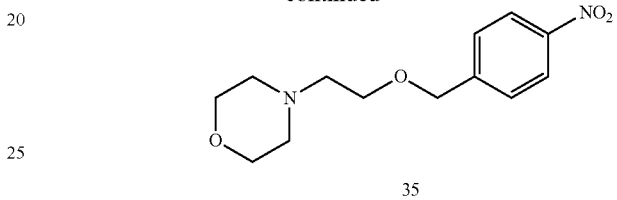

Compound 34 (40.0 g, 0.18 mol) was dissolved in acetic anhydride (200 mL), cooled to 5° C. in an ice-water bath, fuming nitric acid (60 mL) was added dropwise, and stirred at 5° C. for 4 hours. The reaction solution was slowly poured into aqueous sodium carbonate solution to make pH>8, and extracted with ethyl acetate. The organic phase was washed with water and saturated brine, vacuum concentrated, and purified by silica gel column (DCM:MeOH=10:1) to give a colorless oil, namely Compound 35 (30.1 g, yield 62%). Measured: ESI-MS m/z=267 [M+1]$^+$

6.3. Synthesis of Compound 36

Compound 36: 4-((2-morpholinoethoxy)methyl)aniline

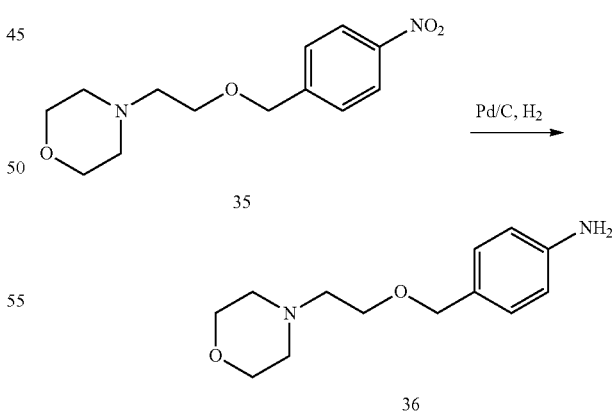

Compound 35 (5.0 g, 0.018 mol) was dissolved in ethyl acetate (200 mL), 10% palladium on carbon (1.0 g) were added, and the system was replaced with hydrogen for 3 times, and stirred at room temperature for 16 hours under hydrogen atmosphere. The reaction solution was filtered, and the filtrate was vacuum concentrated to dryness to give a crude red Compound 36 (4.5 g), which was directly used in the next step. Measured: ESI-MS m/z=237 [M+1]$^+$

6.4. Synthesis of Compound 37

Compound 37

1-(4-((2-morpholinoethoxy)methyl)phenyl)-3-(4-(4,4,5,5-tetramethyl-1,3,2-dioxaborolan-2-yl)phenyl)urea

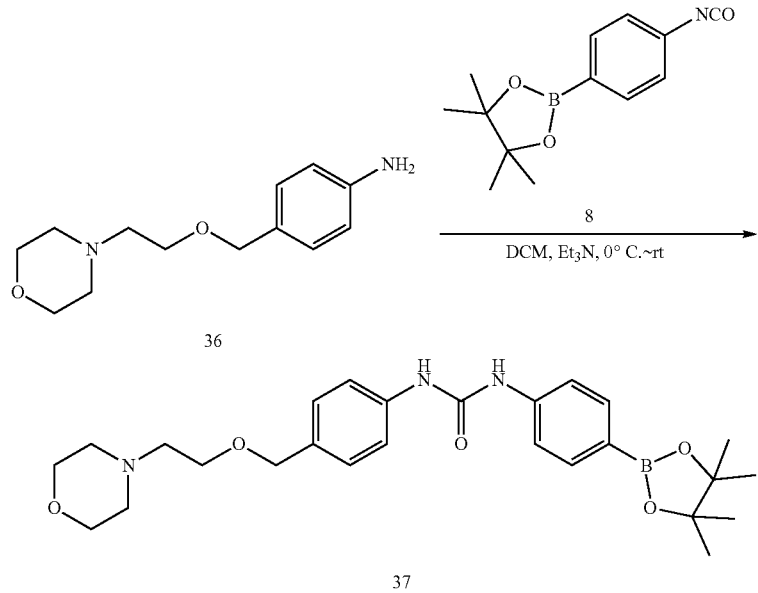

To a dichloromethane solution of Compound 8 (100 mL, from 6.6 g of Compound 7, 30 mmol) was added dropwise a dichloromethane solution of Compound 36 (5.9 g, 25 mmol) in an ice bath. The reaction solution was stirred overnight at room temperature, washed with aqueous sodium bicarbonate solution, washed with water, and the organic phase was vacuum concentrated, and purified by silica gel column (DCM:MeOH=10:1) to give a yellow solid, namely Compound 37 (8.7 g, yield 72.3%). Measured: ESI-MS m/z=482 [M+1]$^+$

6.5. Synthesis of Compound 38

Compound 38

1-(4-(4-cyano-5-fluoro-6-morpholinopyrimidin-2-yl)phenyl)-3-(4-((2-morpholinoethoxy)methyl)phenyl)urea

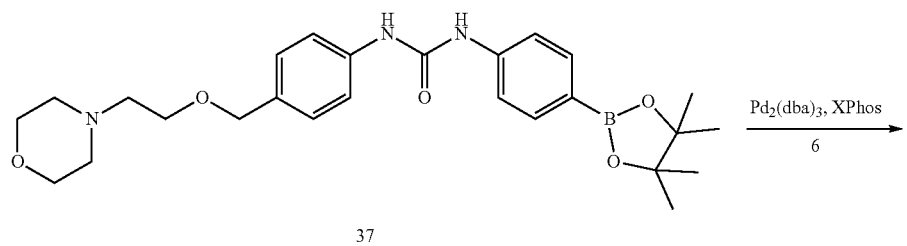

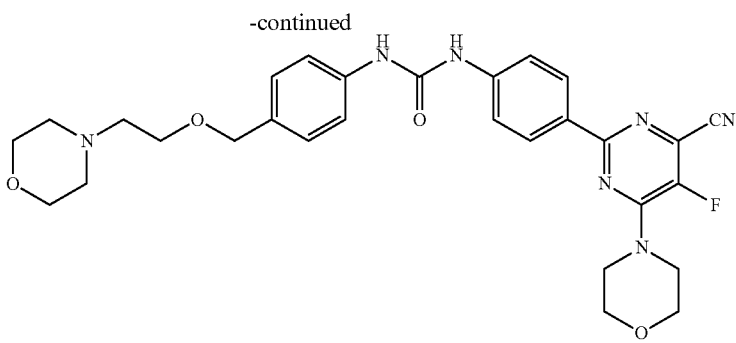

38

Compound 37 (4.0 g, 8.3 mmol) was dissolved in 1,4-dioxane (100 mL) and water (10 mL), then Compound 6 (3.0 g, 12 mmol), sodium bicarbonate (2.5 g, 29.7 mmol), XPhos (600 mg) and Pd$_2$(dba)$_3$ (300 mg) were added. The reaction solution was stirred at 85° C. overnight. After LCMS detection showed the reaction completion, 20 mL of water was added, and the system was extracted with ethyl acetate, and the organic phase was dried over anhydrous sodium sulfate, and filtered, and the filtrate was vacuum concentrated to give a red solid, namely Compound 38 (6.0 g, crude), which was directly used in the next step. Measured: ESI-MS m/z=562 [M+1]$^+$

6.6. Synthesis of Compound I-6

Compound I-6

1-(4-(3-amino-7-morpholino-1H-pyrazolo[4,3-d]pyrimidin-5-yl)phenyl)-3-(4-((2-morpholinoethoxy)methyl)phenyl)urea Compound 38 (5.5 g, crude) was dissolved in 1,4-dioxane (100 mL), hydrazine hydrate (15 mL, 85%) was added, and stirred at 70° C. for 16 h. After LCMS detection showed the reaction completion, 10 mL of water was added, the system was concentrated, precipitated a solid, filtered, and the filter cake was washed with water (10 mL×2), and purified by column chromatography (dichloromethane/methanol=20:1) to give Compound I-6 (900 mg, 19%). Measured: $^1$H NMR (DMSO-d6, 400 MHz): δ 11.76 (s, 1H), 8.81 (s, 1H), 8.71 (s, 1H), 8.31-8.29 (m, 2H), 7.54-7.52 (m, 2H), 7.46-7.44 (m, 2H), 7.25-7.23 (m, 2H), 5.36 (bs, 2H), 4.40 (s, 2H), 3.96 (bs, 3H), 3.76 (s, 4H), 3.55-3.52 (m, 6H), 2.40 (s, 4H). LCMS [mobile phase: from 80% water (0.02% NH$_4$Ac) and 20% CH$_3$CN to 30% water (0.02% NH$_4$Ac) and 70% CH$_3$CN in 6.5 min, finally under these conditions for 0.5 min.] purity is >95%, Rt=2.823 min; MS Calcd.: 573; MS Found: 574 [M+H]$^+$.

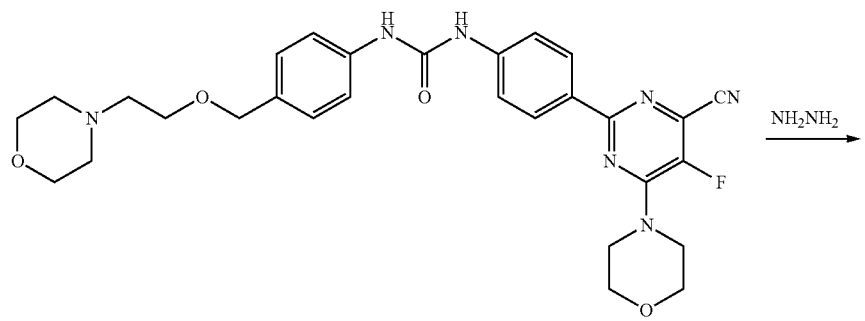

38

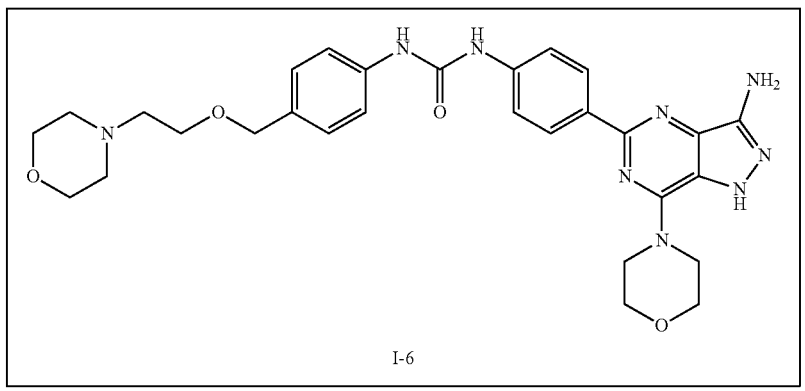

I-6

Embodiment 7: Biological Activity Experiment of the Compounds of the Embodiments PI3-Kinase (human) HTRF™ Assay kit (PI3-Kinase (human) HTRF™ Assay kit detection method is an international general method) was used to detect the half inhibitory concentration of PI3K alpha enzyme ($IC_{50}$ determination)) of the six compounds, namely Compound I-1, Compound I-2, Compound I-3, Compound I-4, Compound I-5, Compound I-6 (in the following experiments, they were respectively given code RMP-D09, RMP-D01, RMP-D02, RMP-D03, RMP-D04, RMP-D05) in the embodiments, and the compound GDC-0941 was used as a positive control. Positive control substance: GDC0941 (Pictilisib)

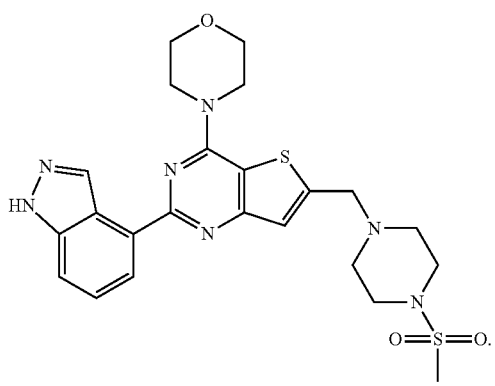

GDC0941 (Pictilisib)

7.1 Materials and Instruments

2104 EnVision® Multilabel Reader (Cat: 2104-0010, PerkinElmer);
384 well opaque black plate (Cat. 6007270, PerkinElmer);
PI3-Kinase (human) HTRF™ Assay kit (Cat. 33-016, Millipore);
4× Reaction Buffer (Cat. 33-002, Millipore); PIP2 1 mM (Cat. 33-004, Millipore); Stop A (Cat. 33-006, Millipore); Stop B (Cat. 33-008, Millipore); DM A (Cat. 33-010, Millipore); DM B (Cat. 33-012, Millipore); DM C (Cat. 33-014, Millipore); PI3k alpha (Cat. 14-602, Millipore); ATP 10 mM (cat PV3227, Invitrogen); DTT 1M (cat D5545, Sigma);
Compounds to be tested: Compound I-1, Compound I-2, Compound I-3, Compound I-4, Compound I-5, Compound I-6 (in the following experiments, they were respectively given codes RMP-D09, RMP-D01, RMP-D02, RMP-D03, RMP-D04, RMP-D05), and GDC-0941.

7.2 Reagent Preparation

1× Reaction Buffer

4× Reaction Buffer was diluted to 1× with dd$H_2O$, and 1M DTT was added to make the final concentration of 5 mM. Prepare fresh before each use. For example, to prepare 10 mL 1× Reaction Buffer, adding 2.5 mL 4× Reaction Buffer, 50 μL 1 M DTT, and 7.45 mL dd$H_2O$. Throughout the experiment, freshly prepared 1× Reaction Buffer was used to prepare ATP working solution, substrate and enzyme mixed working solution, etc.

4× Compound Working Solution

The compound to be tested was dissolved in DMSO to 1 mM as a storage solution, and then diluted with DMSO in a 4-fold ratio for a total of 10 concentration points. 1 μL of each was added to 24 μL 1× Reaction Buffer. 5 μL of each diluted solution was added into a 384-well plate and contained 1% DMSO.

2×PIP2 Working Solution

1× reaction buffer was used to prepare 2×PIP2 working solution to make the final concentration of 20 μM and PIP2 reaction final concentration of 10 μM, for example, to prepare 1 ml 1× reaction buffer/PIP2 working solution, add 20 μL of PIP2 to 980 μL 1× reaction buffer. This working solution should be prepared with 0.1-0.2 ml more to meet the control usage and dead volume.

2×PIP2/Kinase Working Solution

The kinase was diluted with 2×PIP2 working solution, and the concentration of the kinase working solution was 10 ng/well.

Kinase-Free Control (It can be Regarded as 100% Inhibition)

That is, 2×PIP2 working solution.

4×ATP Working Solution 10 mM ATP was diluted to 40 μM with 1× reaction buffer. In a 20 μL kinase reaction system, the concentration of ATP was 10 μM. For example, to prepare 2 ml ATP working solution, take 8 μL 10 mM ATP and add it to 1992 μL 1× reaction buffer.

Stop Solution

Stop A and Stop B were mixed in a ratio of 3:1 and can be used after at least 2 hours at room temperature. The stop solution can be stable for 12 hours at room temperature.

Test Solution

DM C, DM A and DM B were mixed in a ratio of 18:1:1, and can be used after at least 2 hours at room temperature. The test solution can be stable for 12 hours at room temperature.

7.3 Experimental Procedure

| | Reagent | Screening group Kinase + compound | Control group 100% inhibition Kinase-free | 0% inhibition With kinase and no compound |
|---|---|---|---|---|
| Kinase response | 4 × Compound | 5 μL | — | — |
| | 4% DMSO | — | 5 μL | 5 μL |
| | 2 × PIP2 | — | 10 μL | — |
| | 2 × PIP2/kinase | 10 μL | — | 10 μL |
| | 4 × ATP | 5 μL | 5 μL | 5 μL |
| ↓After mixing, incubate at room temperature for 30 minutes |

-continued

| | Screening | Control group | |
|---|---|---|---|
| | group Kinase + | 100% inhibition | 0% inhibition With kinase and |
| Reagent | compound | Kinase-free | no compound |
| Test Stop Solution | 5 μL | 5 μL | 5 μL |
| Test Solution | 5 μL | 5 μL | 5 μL |

↓After mixing, incubate at room temperature for 2 hours
Excitation at 320 nM, and emission signal detection at 665 nm, 620 nm Data Analysis Calculation of the Emission Ratio (ER) of Each Well Emission Ratio (ER)=665 nM Emission signal/620 nm Emission signal
The average emission intensity ratio (Emission Ratio) of the 100% inhibition control is recorded as: $ER_{100\%}$
The average Emission Ratio of the 0% inhibition control is recorded as: $ER_{0\%}$ Calculation of the Inhibition Rate The inhibition rate is calculated with the following formula:

Inhibition rate=$(ER_{sample}-ER_{0\%})/(ER_{100\%}-ER_{0\%})\times$ 100% [$(ER_{positive}-ERsample)/(ERpositive-ERnegative)*100\%$]

7.4 Experimental Results

PI3-Kinase (human) HTRF™ Assay kit was used to detect the inhibition rate of the 6 compounds on PI3K-alpha enzyme at different concentrations, with the concentration of DMSO controlled to 1%, double holes for each concentration, and selecting GDC-0941 as a positive reference substance. The measurement results are shown in FIG. 1. According to the test results, the half inhibitory concentration ($IC_{50}$) of each compound on PI3K-alpha enzyme is summarized in Table 1 below.

TABLE 1 the half inhibitory concentrations ($IC_{50}$)
of the tested compounds on PI3K-alpha

| Compound | $IC_{50}$ (nM) |
|---|---|
| I-1 (RMP-D09) | 10.7 |
| I-2 (RMP-D01) | 89.6 |
| I-3 (RMP-D02) | 89.07 |
| I-4 (RMP-D03) | 108.4 |
| I-5 (RMP-D04) | 228.4 |
| I-6 (RMP-D05) | 40.9 |
| GDC0941 (Pictilisib) | 31.28 |

The above experiments proved the inhibitory effect of the novel pyrazolopyrimidine compound of the present disclosure on phosphatidylinositol 3-kinase (PI3K), indicating that the novel pyrazolopyrimidine compound (including its pharmaceutically acceptable salts, etc.) of the present disclosure is a kind of new PI3K inhibitor. Therefore, it can be used to treat phosphatidylinositol 3-kinase (PI3K)-mediated diseases, and its treatable malignancies include but are not limited to renal carcinoma, liver cancer, colon cancer, gastrointestinal stromal tumor, non-small cell lung cancer, breast cancer, pancreatic cancer, glioma, lymphoma, fibrosarcoma, ovarian cancer, leukemia and prostate cancer, etc.

The other compounds of the present disclosure have basically the same structure as Compound I-1 to Compound I-6, and it can be expected that they have excellent activities comparable to Compound I-1 to Compound I-6. This class of compounds is the world's first new type of compound, which has shown obvious strong activity, and will be used in further new drug research to invent domestically-made innovative drugs, to use in cheap anti-cancer drugs with strong effects and small side effects urgently needed in the market.

The explanation on the above embodiments is only to help understanding of the method and its core concept of the present disclosure. It should be noted that, for those ordinary skilled in the art, various improvements and modifications can be made without depart from the technical principle of the present disclosure, and these improvements and modifications should be covered by the protective scope of the present disclosure.

The invention claimed is:
1. A pyrazolopyrimidine compound represented by Formula (I), or a stereoisomer, a pharmaceutically acceptable salt, a solvate or a crystal thereof,

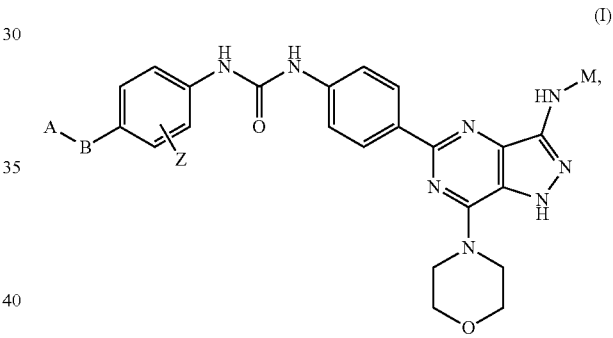

(I)

in the formula, A is selected from the group consisting of —OH, —NH$_2$, —SH,

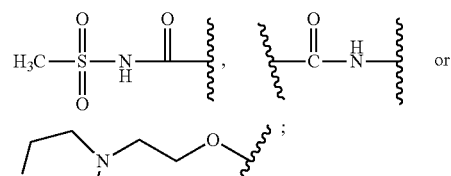

or

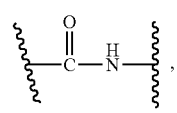

;

B is —C$_n$H$_{2n}$—, n is 1, 2, 3 or 4; wherein, when A is

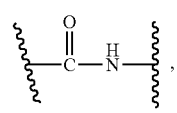

, one end thereof is connected to B, and the other end is connected to a carbon atom on a phenyl ring to which B is connected;

Z is selected from the group consisting of hydrogen, hydroxy, C$_{1-3}$ alkyl, fluorine, chlorine, bromine, or C$_{1-3}$ alkyl substituted by one or more selected from fluorine, chlorine and bromine;

M is H, —CH$_3$ or —CH$_2$CH$_3$.

2. The pyrazolopyrimidine compound represented by Formula (I), or the stereoisomer, the pharmaceutically acceptable salt, the solvate or the crystal thereof according to claim 1, wherein, the structure of the pyrazolopyrimidine compound is represented by the following Formula (I-a):

(I-a)

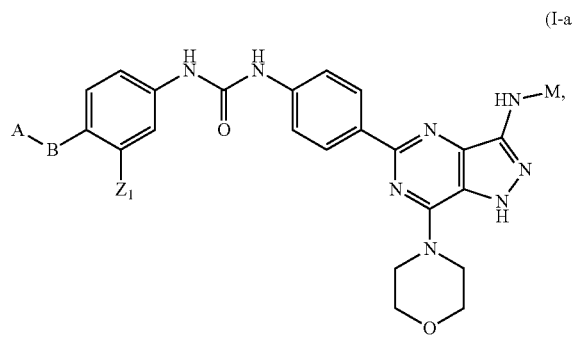

wherein, A, B and M are defined the same as in the preceding claim, and Z$_1$ is selected from the group consisting of hydrogen, hydroxyl, fluorine, chlorine, bromine, methyl, ethyl, isopropyl, trifluoromethyl or pentafluoroethyl.

3. The pyrazolopyrimidine compound represented by Formula (I), or the stereoisomer, the pharmaceutically acceptable salt, the solvate or the crystal thereof according to claim 1, wherein, B is selected from the group consisting of —CH$_2$—, —CH$_2$CH$_2$—, —CH$_2$CH$_2$CH$_2$—, —CH(CH$_3$)—, —CH(CH$_3$)CH$_2$—, —C(CH$_3$)$_2$— or —CH$_2$C(CH$_3$)$_2$—.

4. The pyrazolopyrimidine compound represented by Formula (I), or the stereoisomer, the pharmaceutically acceptable salt, the solvate or the crystal thereof according to claim 1, wherein, when A is

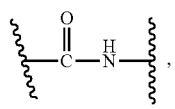

C thereof is connected to B, N is connected to a carbon atom on a phenyl ring to which B is connected, and A, B and the carbon atom to which they are connected together form a 5- to 7-membered ring.

5. The pyrazolopyrimidine compound represented by Formula (I), or the stereoisomer, the pharmaceutically acceptable salt, the solvate or the crystal thereof according to claim 1, wherein, B is —CH$_2$—, and A is —OH,

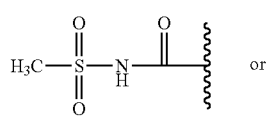 or

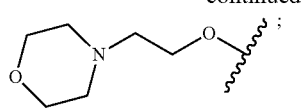

or, B is —C(CH$_3$)$_2$—, and A is —OH or

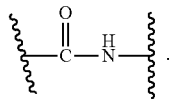.

6. The pyrazolopyrimidine compound represented by Formula (I), or the stereoisomer, the pharmaceutically acceptable salt, the solvate or the crystal thereof according to claim 1, wherein, the pyrazolopyrimidine compound is selected from compounds represented by the following structures:

I-1

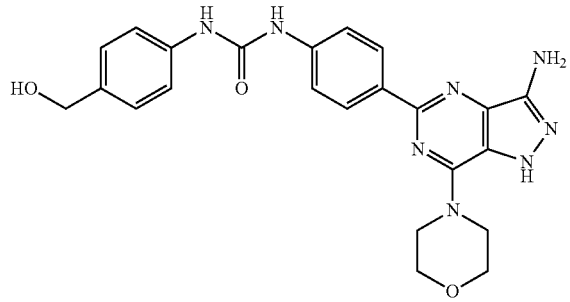

I-2

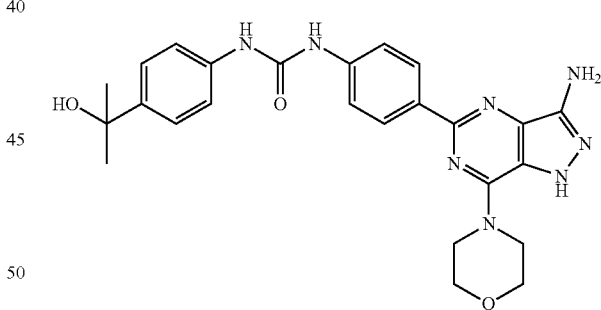

I-3

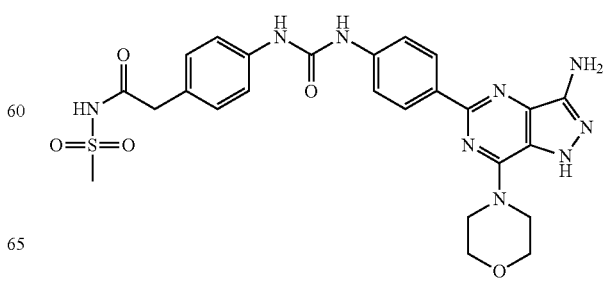

-continued

I-4
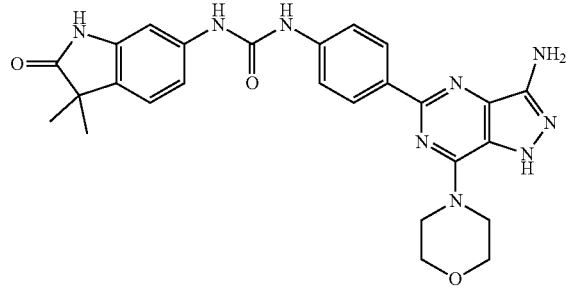

I-5
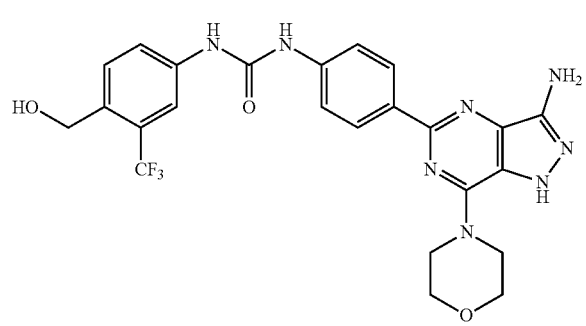

I-6
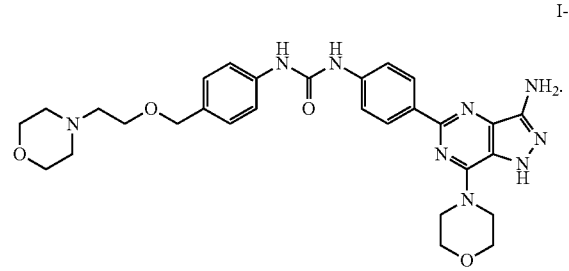

7. A method of treating phosphatidylinositol 3-kinase (PI3K)-mediated diseases in a subject in need thereof, wherein:
the method comprises administering to the subject a therapeutically effective amount of the pyrazolopyrimidine compound represented by Formula (I), or the stereoisomer, the pharmaceutically acceptable salt, the solvate or the crystal thereof of claim 1; and
wherein the phosphatidylinositol 3-kinase (PI3K)-mediated diseases comprise cancer, wherein the cancer comprises renal carcinoma, liver cancer, colon cancer, gastrointestinal stromal tumor, non-small cell lung cancer, breast cancer, pancreatic cancer, glioma, lymphoma, fibrosarcoma, ovarian cancer, leukemia, or prostate cancer.

8. A pharmaceutical composition, wherein, it contains the pyrazolopyrimidine compound represented by Formula (I), or the stereoisomer, the pharmaceutically acceptable salt, the solvate or the crystal thereof according to claim 1, and a pharmaceutical acceptable carrier.

9. The pharmaceutical composition according to claim 8, wherein, the pharmaceutical composition is a composition for treating cancer.

10. An intermediate for preparing the pyrazolopyrimidine compound represented by Formula (I), or the stereoisomer, the pharmaceutically acceptable salt, the solvate or the crystal thereof according to claim 1, wherein, the intermediate has a structure represented by Formula (II):

(II)
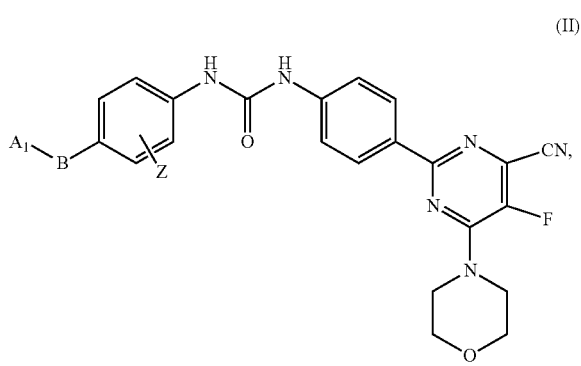

in Formula (II), $A_1$ is tert-butyldimethylsiloxy or $A_1$ is the same as A in Formula (I);
B and Z are respectively the same as B and Z in Formula (I).

11. The intermediate according to claim 10, wherein, the intermediate is selected from compounds represented by the following structures:

(II-1)
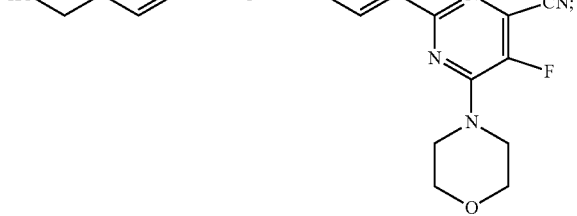

(II-2)
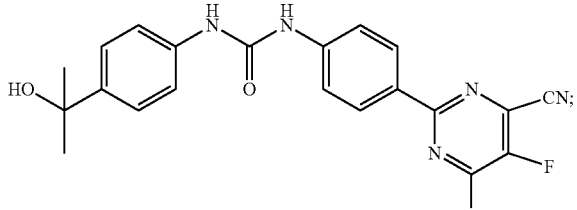

(II-3)
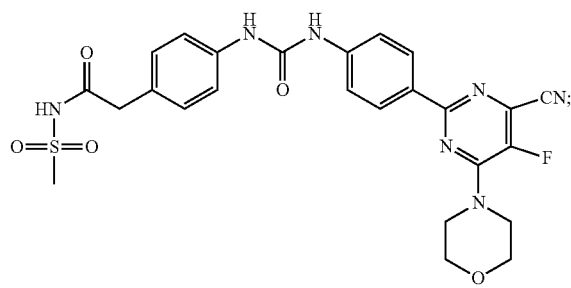

-continued (II-4)
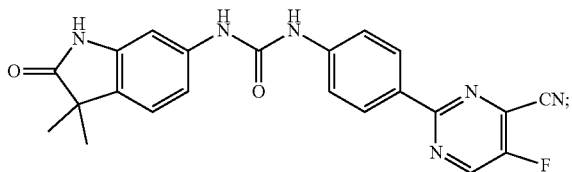

(II-5)
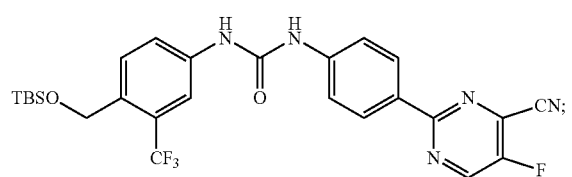

(II-6)
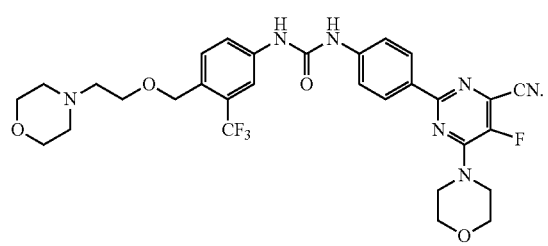

12. A method for preparing the pyrazolopyrimidine compound represented by Formula (I), or the stereoisomer, the pharmaceutically acceptable salt, the solvate or the crystal thereof according to claim 1, wherein, the preparation method comprises a step of reacting the intermediate represented by Formula (II) with hydrazine hydrate, wherein the structure of Formula (II) is (II)
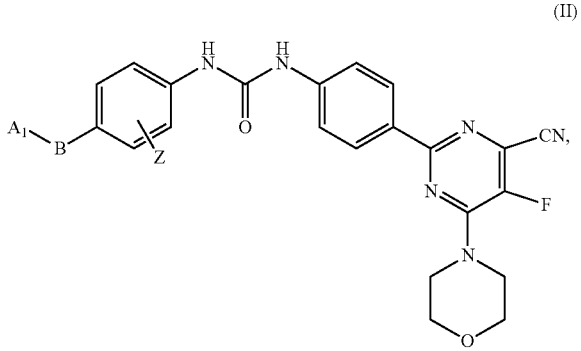

in Formula (II), A₁ is tert-butyldimethylsiloxy or A₁ is the same as A in Formula (I);

B and Z are respectively the same as B and Z in Formula (I).

13. The preparation method according to claim 12, wherein, the reaction of the intermediate represented by Formula (II) with hydrazine hydrate is carried out at 20-100° C.

14. The preparation method according to claim 12, wherein, the intermediate represented by Formula (II) is prepared by reacting

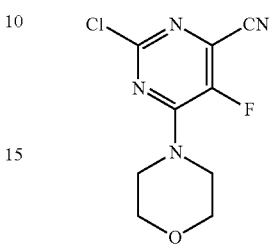

with a compound represented by Formula (III)

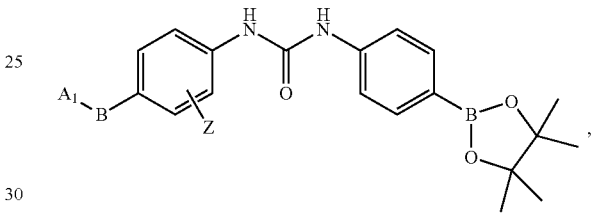

and in Formula (III), A₁, B and Z are defined the same as in Formula (II).

15. The preparation method according to claim 14, wherein, in the process of preparing the intermediate represented by Formula (II), the reaction is carried out under alkaline conditions at a temperature of 30-120° C., and optionally under an inert atmosphere.

16. The preparation method according to claim 15, wherein, the alkaline condition is formed by adding an alkaline substance, and the alkaline substance is selected from the group consisting of potassium acetate, potassium carbonate, potassium phenoxide, potassium phosphate, potassium tert-butoxide, sodium carbonate, sodium bicarbonate, sodium tert-butoxide, sodium methoxide, sodium ethoxide, triethylamine, tri-n-butylamine, diisopropylethylamine, and combinations thereof.

17. The pyrazolopyrimidine compound represented by Formula (I), or the stereoisomer, the pharmaceutically acceptable salt, the solvate or the crystal thereof according to claim 4, wherein, when A is

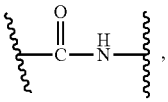

C thereof is connected to B, N is connected to a carbon atom on a phenyl ring to which B is connected, and A, B and the carbon atom to which they are connected together form a 5-membered ring.

18. The preparation method according to claim 13, wherein, the reaction of the intermediate represented by Formula (II) with hydrazine hydrate is carried out at 30-95° C.

19. The preparation method according to claim 13, wherein, the reaction of the intermediate represented by Formula (II) with hydrazine hydrate is carried out at 40-90° C.

20. The preparation method according to claim 19, wherein, the reaction of the intermediate represented by Formula (II) with hydrazine hydrate is carried out at 55-80° C.

21. The preparation method according to claim 19, wherein, the reaction of the intermediate represented by Formula (II) with hydrazine hydrate is carried out at 60-75° C.

\* \* \* \* \*